(12) United States Patent
Terry

(10) Patent No.: US 11,974,053 B2
(45) Date of Patent: Apr. 30, 2024

(54) STEREOSCOPIC IMAGING PLATFORM WITH CONTINUOUS AUTOFOCUSING MODE

(71) Applicant: Alcon Inc., Fribourg (CH)

(72) Inventor: Patrick Terry, Goleta, CA (US)

(73) Assignee: Alcon, Inc., Fribourg (CH)

( * ) Notice: Subject to any disclaimer, the term of this patent is extended or adjusted under 35 U.S.C. 154(b) by 13 days.

(21) Appl. No.: 17/684,851

(22) Filed: Mar. 2, 2022

(65) Prior Publication Data

US 2022/0311947 A1   Sep. 29, 2022

Related U.S. Application Data

(60) Provisional application No. 63/167,406, filed on Mar. 29, 2021.

(51) Int. Cl.
| | |
|---|---|
| *H04N 23/959* | (2023.01) |
| *A61B 90/00* | (2016.01) |
| *G06T 7/593* | (2017.01) |
| *H04N 13/204* | (2018.01) |
| *H04N 13/296* | (2018.01) |
| *H04N 23/67* | (2023.01) |
| *H04N 23/695* | (2023.01) |
| *H04N 13/00* | (2018.01) |

(52) U.S. Cl.
CPC ......... *H04N 23/959* (2023.01); *A61B 90/361* (2016.02); *G06T 7/593* (2017.01); *H04N 13/204* (2018.05); *H04N 13/296* (2018.05); *H04N 23/673* (2023.01); *H04N 23/695* (2023.01); *A61B 90/37* (2016.02); *G06T 2207/10021* (2013.01); *G06T 2207/30004* (2013.01); *H04N 2013/0081* (2013.01)

(58) Field of Classification Search
CPC .................. A61B 90/361; A61B 90/37; G06T 2207/10021; G06T 2207/30004; G06T 7/593
See application file for complete search history.

(56) References Cited

U.S. PATENT DOCUMENTS

| | | | |
|---|---|---|---|
| 9,948,918 B2 * | 4/2018 | Cheng .................. | H04N 13/239 |
| 11,321,914 B1 * | 5/2022 | Fotland .................... | G06T 7/579 |

(Continued)

FOREIGN PATENT DOCUMENTS

| | | |
|---|---|---|
| EP | 2549763 A2 | 1/2013 |
| EP | 2590421 A1 | 5/2013 |

*Primary Examiner* — Peter D Le
(74) *Attorney, Agent, or Firm* — Quinn IP Law

(57) ABSTRACT

A stereoscopic imaging platform includes a stereoscopic camera configured to record left and right images of a target site. A robotic arm is operatively connected to the stereoscopic camera, the robotic arm being adapted to selectively move the stereoscopic camera relative to the target. The stereoscopic camera includes a lens assembly having at least one lens and defining a working distance. The lens assembly has at least one focus motor adapted to move the at least one lens to selectively vary the working distance. A controller is adapted to selectively execute one or more automatic focusing modes for the stereoscopic camera. The automatic focusing modes include a continuous autofocus mode adapted to maintain a focus of the at least one stereoscopic image while the robotic arm is moving the stereoscopic camera and the target site is moving along at least an axial direction.

17 Claims, 8 Drawing Sheets

(56) References Cited

U.S. PATENT DOCUMENTS

| | | | |
|---|---|---|---|
| 11,633,245 B2* | 4/2023 | Kasai | A61B 90/361 |
| | | | 700/259 |
| 2002/0101568 A1* | 8/2002 | Eberl | G02B 27/0172 |
| | | | 351/211 |
| 2006/0025888 A1* | 2/2006 | Gutmann | G06T 7/593 |
| | | | 700/253 |
| 2006/0100642 A1* | 5/2006 | Yang | A61B 34/70 |
| | | | 606/130 |
| 2007/0156017 A1* | 7/2007 | Lamprecht | A61B 1/00194 |
| | | | 600/102 |
| 2012/0033051 A1* | 2/2012 | Atanassov | G06T 7/593 |
| | | | 348/E13.074 |
| 2012/0120202 A1* | 5/2012 | Yoon | H04N 13/239 |
| | | | 348/E13.074 |
| 2018/0068462 A1* | 3/2018 | Wakai | H04N 13/246 |
| 2018/0176483 A1* | 6/2018 | Knorr | H04N 5/2723 |
| 2018/0289428 A1* | 10/2018 | Lee | G02B 21/365 |
| 2018/0324349 A1* | 11/2018 | Kim | G06V 10/147 |
| 2019/0089886 A1* | 3/2019 | Hattori | H04N 23/695 |
| 2019/0254757 A1* | 8/2019 | Piron | A61B 5/742 |
| 2019/0327394 A1* | 10/2019 | Ramirez Luna | H04N 23/51 |
| 2020/0054401 A1* | 2/2020 | Yu | B25J 9/1633 |
| 2021/0326694 A1* | 10/2021 | Wang | G06T 7/593 |
| 2022/0272272 A1* | 8/2022 | Keenan | A61B 34/30 |
| 2022/0383531 A1* | 12/2022 | Santini | H04N 13/239 |

* cited by examiner

STEREOSCOPIC IMAGING PLATFORM WITH CONTINUOUS AUTOFOCUSING MODE

CROSS REFERENCE TO RELATED APPLICATION

The present application claims the benefit of priority to U.S. Provisional Application No. 63/167,406 filed Mar. 29, 2021, which is hereby incorporated by reference in its entirety.

INTRODUCTION

The present disclosure relates generally to a stereoscopic imaging platform. More specifically, the disclosure relates to automatic focusing modes in a robotic-assisted stereoscopic imaging platform. Various imaging modalities are commonly employed to image various parts of the human body. For example, medical procedures such as surgery may require the acquisition of images in real-time, images that are focused. Automatic focus brings an object of interest in a scene into focus, by appropriately moving portions of the lens assembly in the imaging device. However, performing automatic focus in a stereoscopic imaging device is challenging. A stereoscopic imaging device generally includes multiple lenses each having a separate image sensor. The lenses are arranged such that each has a field of view of a scene that is slightly shifted from the other lenses, such as a left image from a left lens and a right image from a right lens. Because of the differences in perspective, the focusing of the lenses needs to be coordinated so that each lens focuses on the same object. If not, the lenses may simultaneously focus on different objects in the scene, reducing image quality. This challenge is greater when the stereoscopic imaging device is assisted by a robotic system that is capable of moving the imaging device or camera while the image is being acquired.

SUMMARY

Disclosed herein is a stereoscopic imaging platform for imaging a target site. The stereoscopic imaging platform includes a stereoscopic camera configured to record left and right images of the target site for producing at least one stereoscopic image of the target site. A robotic arm is operatively connected to the stereoscopic camera, the robotic arm being adapted to selectively move the stereoscopic camera relative to the target. The stereoscopic camera includes a lens assembly having at least one lens and defining a working distance. The lens assembly has at least one focus motor adapted to move the at least one lens to selectively vary the working distance. A controller is in communication with the stereoscopic camera and has a processor and tangible, non-transitory memory on which instructions are recorded. The controller is adapted to selectively execute one or more automatic focusing modes for the stereoscopic camera. The automatic focusing modes include a continuous autofocus mode adapted to maintain a focus of the at least one stereoscopic image while the robotic arm is moving the stereoscopic camera and the target site is moving along at least an axial direction.

The controller is configured to determine a change in height of the stereoscopic camera from an initial camera position, the change in the height being defined as a displacement in position of the stereoscopic camera along the axial direction. The controller is configured to determine a change in target depth from an initial target position, the change in the target depth being defined as the displacement in position of the target site along the axial direction.

Determining the change in the target depth includes obtaining a disparity signal, including an initial target disparity value and a current disparity value, and executing a closed-loop control module to minimize a difference between the current disparity value and the initial target disparity, via the controller. The change in the target depth may be based on the difference between the current disparity value and the initial target disparity.

The closed-loop control module may be at least one of a proportional-derivative control module, a proportional-integral control module and a proportional-integral-derivative control module. The closed-loop control module may be a proportional-integral-derivative control module defining a proportional constant, an integral constant and a derivative constant. The change in the target depth may be determined as $[Kp(Rc-Rt)+Ki\int(Rc-Rt)dt-Kd*dRc/dt]$, where Rc is the current disparity value, Rt is the initial target disparity value, t is time, Kp is the proportional constant, Ki is the integral constant, and Kd is the derivative constant.

The controller may be configured to obtain the disparity signal by isolating an identifiable region in the left image and isolating a second region in the right image. The second region includes coordinates of the identifiable region and is larger than the identifiable region. A template match is performed to obtain a pixel offset, the pixel offset being a horizontal displacement of the identifiable region in the left image and the identifiable region in the right image. The disparity signal is obtained as the pixel offset at an optimal location of the template match.

The controller is configured to calculate an updated focal length based in part on the change in the height of the stereoscopic camera and the change in the target depth. Calculating the updated focal length may include obtaining the updated focal length F as a function of a first variable Zbase, a second variable z0 and a third variable z3 such that:

$$F = \left(\frac{Z_{base} - z0}{z3}\right).$$

The first variable Zbase is a respective axial component of a current location of the target site in a robotic base frame. The robotic base frame is transformable to a camera coordinate frame via a homogenous transformation matrix, the homogenous transformation matrix being composed of a rotational matrix and a translation vector. The second variable z0 is the respective axial component of the translation vector and the third variable z3 is the respective axial component of a column of the rotational matrix.

The controller is configured to calculate motor commands for the at least one focus motor corresponding to the updated focal length. The controller is configured to transmit the motor commands to the at least one focus motor such that the working distance corresponds to the updated focal length. When movement of the robotic arm is no longer detected, the controller is configured to determine the motor commands for the at least one focus motor corresponding to a maximum sharpness position.

The maximum sharpness position may be based on one or more sharpness parameters, including a sharpness signal, a maximum sharpness signal and a derivative over time of the maximum sharpness. The derivative of the maximum sharpness reaches a maximum at a first position, the derivative of the maximum sharpness moving from the first position and settling at approximately zero at a second position. The maximum sharpness position is defined as the first position. The sharpness signal may be defined as a contrast between respective edges of an object in the at least one stereoscopic image. The maximum sharpness signal may be defined as a largest sharpness value observed during a scan period.

The at least one stereoscopic image includes one or more image frames. The sharpness signal may be obtained by calculating a variance of a Laplacian of a Gaussian Blur of the one or more image frames. When movement of the robotic arm is no longer detected, the controller is configured to command the focus motor to the maximum sharpness position.

Disclosed herein is a robotic imaging platform for imaging a target site. The robotic imaging platform includes a stereoscopic camera configured to record left and right images of the target site for producing at least one stereoscopic image of the target site. A robotic arm is operatively connected to the stereoscopic camera, the robotic arm being adapted to selectively move the stereoscopic camera relative to the target site. The stereoscopic camera includes a lens assembly having at least one lens and defining a working distance, the lens assembly having at least one focus motor adapted to move the at least one lens to selectively vary the working distance. A controller is in communication with the stereoscopic camera and having a processor and tangible, non-transitory memory on which instructions are recorded. The controller is adapted to selectively execute one or more automatic focusing modes for the stereoscopic camera, the one or more automatic focusing modes including a continuous autofocus mode. The continuous autofocus mode is adapted to maintain a focus of the at least one stereoscopic image while the robotic arm is moving the stereoscopic camera and the target site is moving along at least an axial direction.

The continuous autofocus mode is adapted to determine respective deviations from a set of starting values, the set of starting values including an initial camera position and an initial target position. The automatic focusing modes includes at least one of a disparity mode and a sharpness control mode. The set of starting values is obtained from at least one of the disparity mode and the sharpness control mode executed prior to the continuous autofocus mode.

The respective deviations include a change in height of the stereoscopic camera from the initial camera position, the change in the height being defined as a displacement in position of the stereoscopic camera along the axial direction. The respective deviations include a change in target depth from the initial target position, the change in the target depth being defined as the displacement in position of the target site along the axial direction.

The controller is configured to calculate an updated focal length based in part on the change in the height of the stereoscopic camera and the change in the target depth. The change in the target depth is based in part on a difference between a current disparity value and an initial target disparity, the set of starting values including the initial target disparity.

When movement of the robotic arm is no longer detected, the controller is configured to determine motor commands for the at least one focus motor corresponding to a maximum sharpness position. The maximum sharpness position may be based on one or more sharpness parameters, including a sharpness signal, a maximum sharpness signal and a derivative over time of the maximum sharpness.

The above features and advantages and other features and advantages of the present disclosure are readily apparent from the following detailed description of the best modes for carrying out the disclosure when taken in connection with the accompanying drawings.

Figure 1:
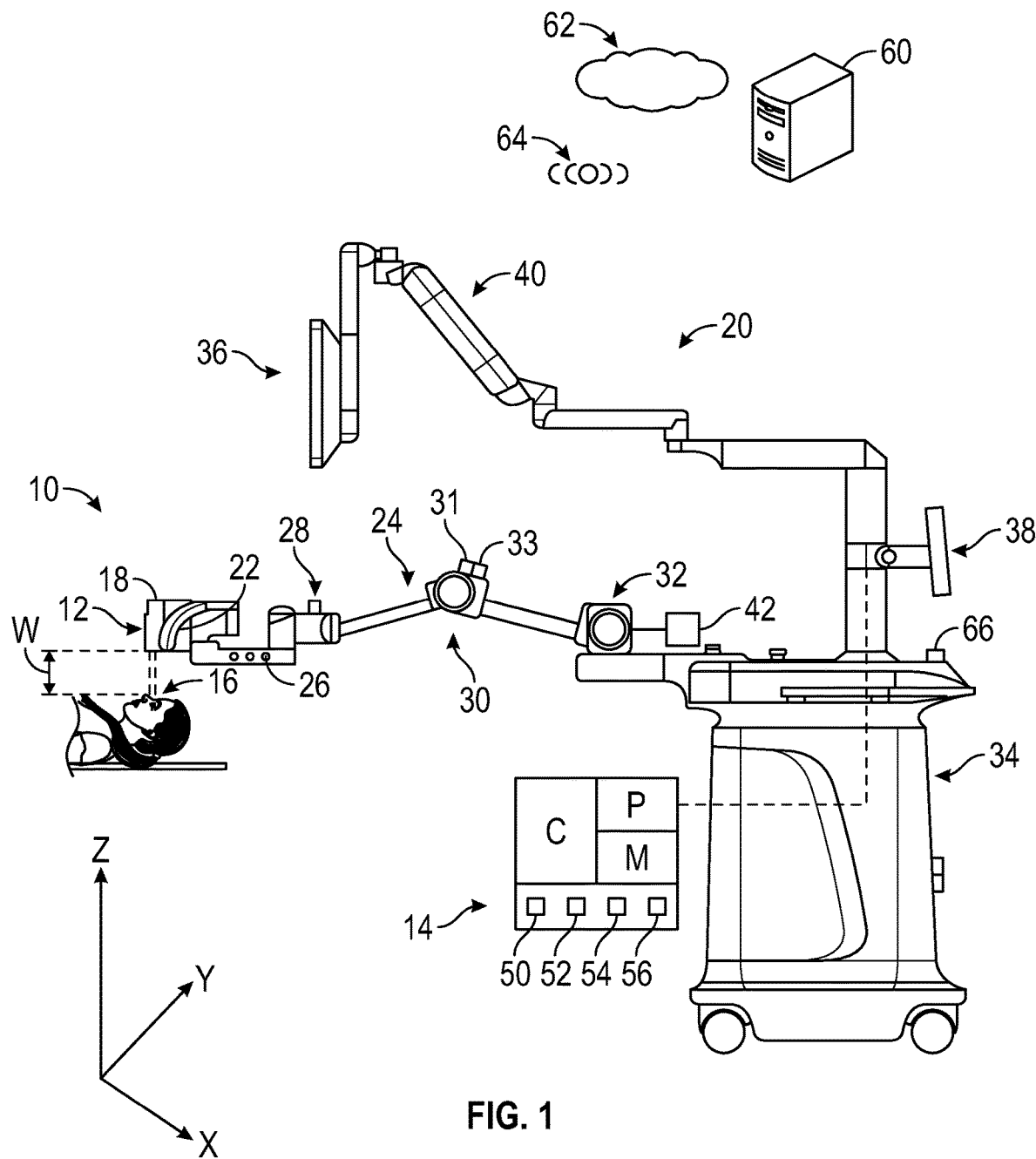
FIG. 1 is a schematic fragmentary diagram of a stereoscopic imaging platform having a stereoscopic camera with one or more autofocusing modes and a controller.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Referring to the drawings, wherein like reference numbers refer to like components, FIG. 1 schematically illustrates a stereoscopic imaging platform 10 having a stereoscopic camera 12 with one or more automatic focusing modes 14. The stereoscopic imaging platform 10 is configured to image a target site 16. Referring to FIG. 1, the stereoscopic camera 12 is at least partially located in a head unit 18 of a housing assembly 20, with the head unit 18 configured to be at least partially directed towards the target site 16. The stereoscopic camera 12 is configured to record first and second images of the target site 16, which may be employed to generate a live two-dimensional stereoscopic view of the target site 16. The target site 16 may be an anatomical location on a patient, a laboratory biological sample, calibration slides/templates, etc.

Referring to FIG. 1, at least one selector 22 may be mounted on the head unit 18 for selecting specific features of the stereoscopic camera 12, such as magnification, focus and other features. The selector 22 may be employed to enable an operator to manually position the head unit 18. The stereoscopic imaging platform 10 may include a robotic arm 24 operatively connected to and configured to selectively move the head unit 18. Referring to FIG. 1, the head unit 18 may be mechanically coupled to the robotic arm 24 via a coupling plate 26. The operator may position and orient the stereoscopic camera 12 with assistance from the robotic arm 24. A sensor 28 may be operatively connected to the robotic arm 24 and/or coupling plate 26. The sensor 28 is configured to detect forces and/or torque imparted by an operator for moving the stereoscopic camera 12.

The robotic arm 24 may include one or more joints, such as first joint 30 and second joint 32, configured to provide further degrees of positioning and/or orientation of the head unit 18. The data from the sensor 28 may be employed to determine which joints of the robotic arm 24 should be rotated and how quickly the joints should be rotated, in order to provide assisted movement of the stereoscopic camera 12 that corresponds to the forces/torques provided by the operator. Referring to FIG. 1, a respective joint motor (such as joint motor 31) and a respective joint sensor (such as joint sensor 33), may be coupled to each joint. The joint motor 31 is configured to rotate the first joint 30 around an axis, while the joint sensor 33 is configured to transmit the position (in 3D space) of the first joint 30.

Referring to FIG. 1, the stereoscopic imaging platform 10 includes a controller C having at least one processor P and at least one memory M (or non-transitory, tangible computer readable storage medium) on which are recorded instructions for executing one or more sub-routines or methods. The memory M can store controller-executable instruction sets, and the processor P can execute the controller-executable instruction sets stored in the memory M.

Referring to FIG. 1, the robotic arm 24 may be controlled via the controller C and/or an integrated processor, such as a robotic arm controller 42. The robotic arm 24 may be selectively operable to extend a viewing range of the stereoscopic camera 12 along an X-axis, a Y-axis and a Z-axis. The head unit 18 may be connected to a cart 34 having at least one display medium (which may be a monitor, terminal or other form of two-dimensional visualization), such as first and second displays 36 and 38 shown in FIG. 1. Referring to FIG. 1, the controller C may be configured to process signals for broadcasting on the first and second displays 36 and 38. The housing assembly 20 may be self-contained and movable between various locations. The image stream from the stereoscopic camera 12 may be sent to the controller C and/or a camera processor (not shown), which may be configured to prepare the image stream for viewing. For example, the controller C may combine or interleave first and second video signals from the stereoscopic camera 12 to create a stereoscopic signal. The controller C may be configured to store video and/or stereoscopic video signals into a video file and stored to memory M. The first and second displays 36 and 38 may incorporate a stereoscopic display system, with a two-dimensional display having separate images for the left and right eye respectively. To view the stereoscopic display, a user may wear special glasses that work in conjunction with the first and second displays 36, 38 to show the left view to the user's left eye and the right view to the user's right eye.

Referring to FIG. 1, the first display 36 may be connected to the cart 34 via a flexible mechanical arm 40 with one or more joints to enable flexible positioning. The flexible mechanical arm 40 may be configured to be sufficiently long to extend over a patient during surgery to provide relatively close viewing for a surgeon. The first and second displays 36, 38 may include any type of display, such as a high-definition television, an ultra high-definition television, smart-eyewear, projectors, one or more computer screens, laptop computers, tablet computers, and/or smartphones and may include a touchscreen.

The stereoscopic camera 12 is configured to acquire stereoscopic images of the target site 16, which may be presented in different forms, including but not limited to, captured still images, real-time images and/or digital video signals. "Real-time" as used herein generally refers to the updating of information at the same rate as data is received. More specifically, "real-time" means that the image data is acquired, processed, and transmitted at a high enough data rate and a low enough delay that when the data is displayed, objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $\frac{1}{30}^{th}$ second of delay.

The controller C is adapted to selectively execute one or more automatic focusing modes 14 ("one or more" omitted henceforth) for the stereoscopic camera 12. Each of the automatic focusing modes 14 may be selectively initiated by a user. The automatic focusing modes 14 leverage the two available images (left and right) of the stereoscopic camera 12 to allow a user to transition the image from unfocused to focused, without requiring laborious manual focusing.

The automatic focusing modes 14 may be used on any stereoscopic visualization device with a working distance W that is variable, e.g., that is changeable. FIG. 1 shows a working distance W, which may be defined as the distance between a reference plane and the focal plane of the target site 16. The working distance W accordingly sets a plane of the target site 16 or scene that is in focus. In the example shown in FIGS. 1-2, the reference plane is an outer surface of the front working distance lens 104. The working distance W may correspond to an angular field-of-view, where a longer working distance results in a wider field-of-view or larger viewable area.

Referring to FIG. 1, the automatic focusing modes 14 may include a disparity mode 50, a sharpness control mode 52, a target locking mode 54 and a continuous autofocus mode 56. Based in part on initial robotic arm input and dynamic image feedback, the automatic focusing modes 14 automatically adjust the working distance W to achieve improved image quality in a variety of situations. The controller C may be adapted to provide an application programming interface (API) for starting and stopping each of the automatic focusing modes 14. Example implementations of the disparity mode 50, sharpness control mode 52, target locking mode 54 and continuous autofocus mode 56 are described below with respect to FIGS. 4, 7, 9 and 11, respectively (as methods 200, 400, 600 and 700).

The disparity mode 50 is adapted to use a disparity signal as a feedback signal to control adjustments in the working distance W during the automatic focusing process. The disparity signal reflects a horizontal displacement between a point of interest in the left-view image and the same point of interest in the right-view image. The sharpness control mode 52 improves the overall image when the stereoscopic camera 12 is in focus and reduces poor image quality due to disparity variance. The sharpness control mode 52 is adapted to use disparity signal as well as multiple sharpness parameters (e.g., sharpness, maximum sharpness and derivative of maximum sharpness). In the disparity mode 50 and sharpness control mode 52, the robotic arm 24 and the target site 16 are fixed in location, as indicated in Table I below.

TABLE I

| | Disparity Mode | Sharpness Control Mode | Target Locking Mode | Continuous Autofocus Mode |
|---|---|---|---|---|
| Target | Fixed | Fixed | Fixed | Moving |
| Robotic Arm | Fixed | Fixed | Moving | Moving |

The target locking mode 54 is adapted to maintain focus in an image while the robotic arm 24 is moving the stereoscopic camera 12 and the target site 16 is fixed. The continuous autofocus mode 56 is adapted to keep the image in focus as both the robotic arm 24 and the target site 16 move. The continuous autofocus mode 56 converges to a maximum sharpness value when the robotic arm 24 has stopped moving.

The controller C of FIG. 1 is specifically programmed to execute the blocks of the methods 200, 400, 600 and 700 (discussed in detail below with respect to FIGS. 4, 7, 9 and 11, respectively) and may include or otherwise have access to information downloaded from remote sources and/or executable programs. Referring to FIG. 1, the controller C may be configured to communicate with a remote server 60 and/or a cloud unit 62, via a network 64. The remote server 60 may be a private or public source of information maintained by an organization, such as for example, a research institute, a company, a university and/or a hospital. The cloud unit 62 may include one or more servers hosted on the Internet to store, manage, and process data.

The network 64 may be a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data. The network 64 may be a Wireless Local Area Network (LAN) which links multiple devices using a wireless distribution method, a Wireless Metropolitan Area Network (MAN) which connects several wireless LANs or a Wireless Wide Area Network (WAN) which covers large areas such as neighboring towns and cities. Other types of connections may be employed.

I. Optical Components of Stereoscopic Camera

Figure 2:
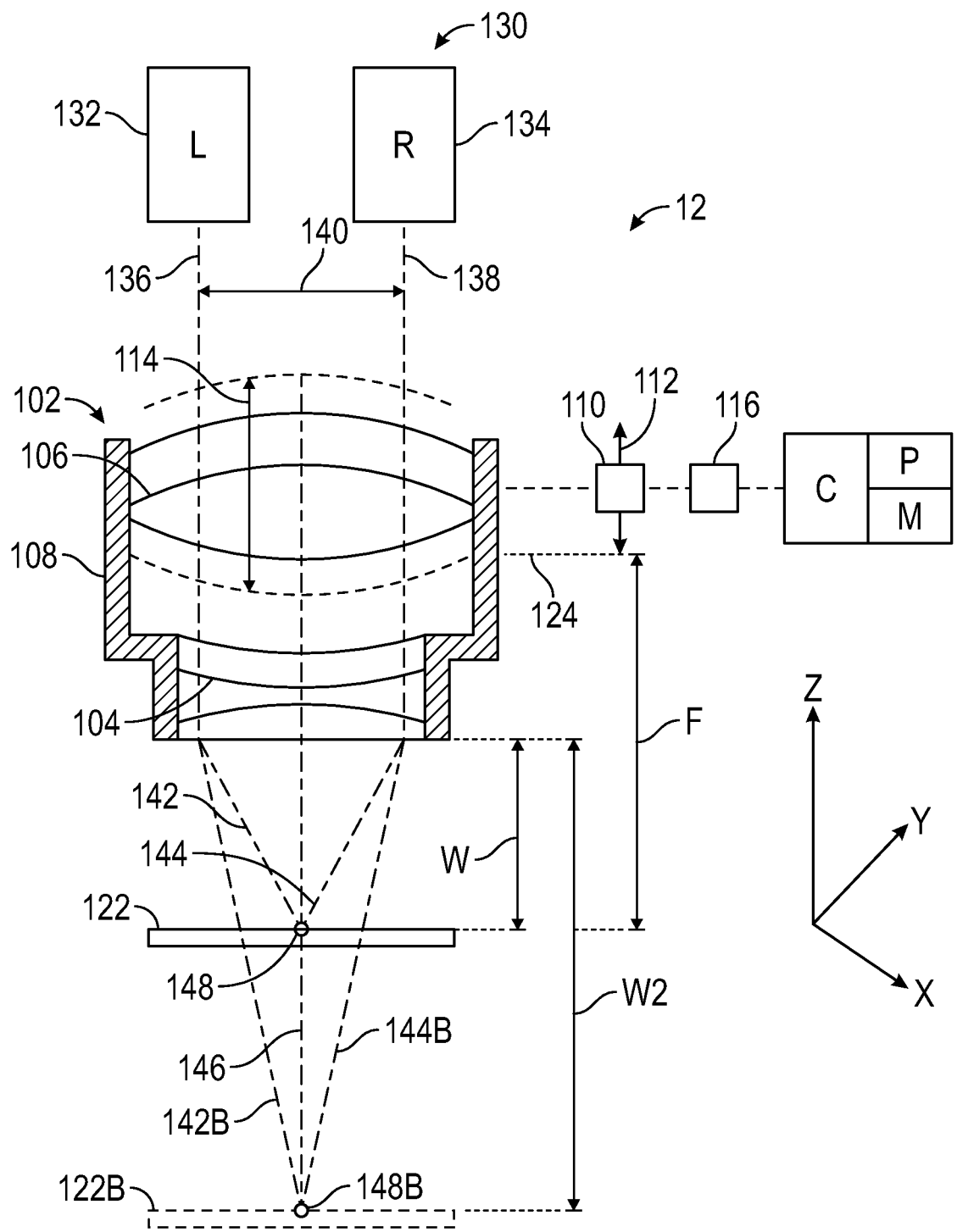
FIG. 2 is a schematic diagram of a portion of the stereoscopic camera of FIG. 1.
Figure 3:
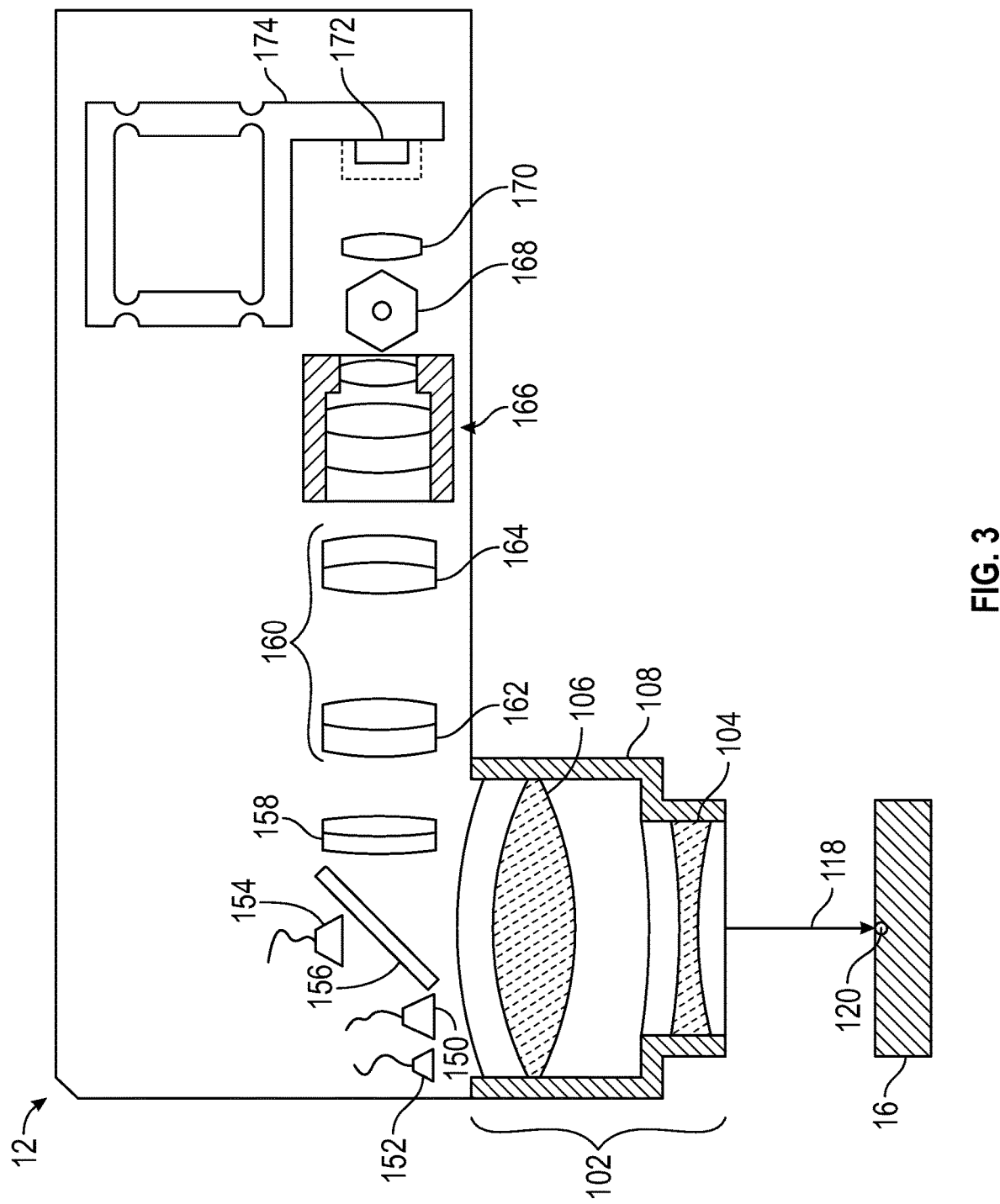
FIG. 3 is a schematic diagram of another portion of the stereoscopic camera of FIG. 1.

Presented in FIGS. 2-3 are example optical components of the stereoscopic camera 12. It is to be understood that other optical components or devices available to those skilled in the art may be employed. Referring now to FIG. 2, a schematic view of a portion of the stereoscopic camera 12 is shown. Images from the target site 16 are received at the stereoscopic camera 12 via an optical assembly 102, shown in FIGS. 2-3. Referring to FIGS. 2-3, the optical assembly 102 includes a front working distance lens 104 and a rear working distance lens 106, within a housing 108.

Referring to FIG. 2, a focal plane 122 is located at a distance equal to the focal length F from a principal plane 124 of the optical assembly 102. Visualization of an object with the stereoscopic camera 12 above or below the focal plane 122 diminishes a focus of the object. It may be difficult to gauge the location of the principal plane 124, so a distance from the bottom surface of the housing 108 to the focal plane 122 is generally designated as the working distance W. The working distance W accurately sets a plane of the target site 16 or scene that is in focus.

The optical assembly 102 is configured to provide a variable working distance W (see FIG. 1) for the stereoscopic camera 12. Referring to FIG. 2, the controller C is adapted to selectively command a focus motor 110 to change the spacing between the rear working distance lens 106 and the front working distance lens 104. The focus motor 110 is movable (for example, along direction 112) to vary the working distance W of the optical assembly 102. As noted above, the working distance W may be referred to as the distance from the stereoscopic camera 12 to a reference plane where the target site 16 is in focus. In some embodiments, the working distance W is adjustable from 200 to 450 mm by moving the rear working distance lens 106 via the focus motor 110.

Movement of the rear working distance lens 106 relative to the front working distance lens 104 also changes the focal length F. In some embodiments, the focal length F is the distance between the rear working distance lens 106 and the front working distance lens 104 plus one-half the thickness of the front working distance lens 104. The focal length F that is achievable is bounded by the maximum and minimum working distance permitted by the hardware. In one example, the focus motor 110 is an electric motor. However, the focus motor 110 may be any type of linear actuator, such as a stepper motor, a shape memory alloy actuator or other type of actuator available to those skilled in the art.

In the embodiment shown, the rear working distance lens 106 is movable along a direction 114 (Z-axis here) while the front working distance lens 104 is stationary. However, it is understood that the front working distance lens 104 may be movable or both the front working distance lens 104 and rear working distance lens 106 may be movable. The focus motor 110 may be selectively operable through the controller C and/or a motor controller 116. The stereoscopic camera 12 may include additional focus motors to independently move the front and rear lenses. The magnification of the optical assembly 102 may vary based on the working distance W. For example, the optical assembly 102 may have a magnification of 8.9× for a 200 mm working distance and a magnification of 8.75× for a 450 mm working distance.

In some embodiments, the front working distance lens 104 is composed of a plano-convex lens and/or a meniscus lens. The rear working distance lens 106 may comprise an achromatic lens. In examples where the optical assembly 102 includes an achromatic refractive assembly, the front working distance lens 104 may include a hemispherical lens and/or a meniscus lens. The rear working distance lens 106 may include an achromatic doublet lens, an achromatic doublet group of lenses, and/or an achromatic triplet lens. The optical assembly 102 may include other types of refractive or reflective assemblies and components available to those skilled in the art.

Referring to FIG. 2, imaging an object at the focal plane 122 develops a conjugate image located at infinity from a back or rear of the optical assembly 102. The optical assembly 102 is configured to provide left and right views of the target site 16, via an optical device 130. In some embodiments, the optical device 130 includes left and right optical units 132, 134 having respective sensors and optical devices. As shown in FIG. 2, the left and right optical units 132, 134 respectively generate a left optical path 136 and a right optical path 138, which are two parallel optical paths within the housing 108. The left and right optical units 132, 134 are transversely separated by a distance 140. In some embodiments, the distance 140 is between about 58 to 70 mm. External to the housing 108, the left optical path 136 and the right optical path 138 extend into a left optical axis 142 and a right optical axis 144, respectively, in slightly different directions from an optical axis 146 of the optical assembly 102. The left optical axis 142 and the right optical axis 144 coincide at the center of the field of view, at an image point 148. The image point 148 may be referred to as the "tip" of the stereoscopic camera 12 at the focal plane 122.

Adjusting the relative positions of the front working distance lens 104 and rear working distance lens 106 creates a new working distance W2, that is located at the position of a new focal plane 122B. Referring to FIG. 2, the movement of the rear working distance lens 106 causes a realignment of the left optical axis 142B and the right optical axis 144B, resulting in a relocated tip 148B of the stereoscopic camera 12.

Together, the front working distance lens 104 and the rear working distance lens 106 are configured to provide an infinite conjugate image for providing an optimal focus for downstream optical image sensors. In other words, an object located exactly at the focal plane of the target site 16 will have its image projected at a distance of infinity, thereby being infinity-coupled at a provided working distance. Generally, the object appears in focus for a certain distance along the optical path from the focal plane. However, past the certain threshold distance, the object begins to appear fuzzy or out of focus.

The optical assembly 102 shown in FIGS. 2-3 provides an image of the target site 16 for both the left and right optical paths 136, 138. In alternative embodiments, the optical assembly 102 may include a separate left and a separate right front working distance lens 104 and separate left and a separate right rear working distance lens 106. Further, each of the rear working distance lenses 106 may be independently adjustable.

Referring now to FIG. 3, a schematic side view of another portion of the stereoscopic camera 12 is shown. The elements shown in FIG. 3 may be part of either the left optical path 136 or the right optical path 138 (see FIG. 2), which are generally identical with respect to the arrangement of elements. Referring to FIG. 3, to illuminate the target site 16, the stereoscopic camera 12 may include one or more lighting sources such as a first light source 150, a second light source 152, and a third light source 154. In other examples, the stereoscopic camera 12 may include additional or fewer light sources. Light generated by the lighting sources interacts and reflects off the target site 16, with some of the light being reflected to the optical assembly 102. Alternatively, the stereoscopic camera 12 may employ external light sources or ambient light from the environment.

In one example, the first light source 150 is configured to output light in the visible part of the electromagnetic spectrum and the second light source 152 is configured to output near-infrared light that is primarily at wavelengths slightly past the red part of the visible spectrum. The third light source 154 may be configured to output near-ultraviolet light that is primarily at wavelengths in the blue part of the visible spectrum. The brightness of the generated light may be controlled by the controller C and/or respective microcontrollers linked to the respective sources. In some embodiments, the light from the third light source 154 is reflected by a deflecting element 156 to the optical assembly 102 using an epi-illumination setup. The deflecting element 156 may be a beam splitter, for example. The deflecting element 156 may be coated or otherwise configured to reflect only light beyond the near ultraviolet wavelength range, thereby filtering the near ultraviolet light.

Referring to FIG. 3, the deflecting element 156 may be configured to transmit a certain wavelength of light from the third light source 154 to the target site 16 through the optical assembly 102. The deflecting element 156 is also configured to reflect light received from the target site 16 to downstream optical elements, including a front lens set 158 for zooming and recording. In some embodiments, the deflecting element 156 may filter light received from the target site 16 through the optical assembly 102 so that light of certain wavelengths reaches the front lens set 158. The deflecting element 156 may include any type of mirror or lens to reflect light in a specified direction. In one example, the deflecting element 156 includes a dichroic mirror or filter, which has different reflection and transmission characteristics at different wavelengths.

Referring to FIG. 3, the stereoscopic camera 12 may include one or more zoom lenses to change a focal length and angle of view of the target site 16 to provide zoom magnification. In the example shown, the zoom lenses include a front lens set 158, a zoom lens assembly 160, and a lens barrel set 166. The front lens set 158 may each include respective positive converging lenses (for the right and left optical paths) to direct light from the deflecting element 156 to respective lenses in the zoom lens assembly 160. The lateral position of the front lens set 158 may define a beam from the optical assembly 102 and the deflecting element 156 that is propagated to the zoom lens assembly 160. The front lens set 158 may include lenses with adjustable radial and axial positions.

Referring to FIG. 3, the zoom lens assembly 160 may form an afocal zoom system for changing the size of a field-of-view (e.g., a linear field-of-view) by changing the size of the light beam propagated to the lens barrel set 166. The zoom lens assembly 160 may include a front zoom lens set 162 with respective right and left front zoom lenses. The zoom lens assembly 160 may include a rear zoom lens set 164 with respective right and left front zoom lenses. The front zoom lens set 162 may include positive converging lenses while the rear zoom lens set 164 may include negative diverging lenses. In some embodiments, the lens barrel set 166 may be fixed radially and axially within the housing 108. In other examples, the lens barrel set 166 may be movable axially along the optical path to provide increased magnification. Additionally, some or all of the respective elements in the front lens set 158, the front zoom lens set 162, and/or the rear zoom lens set 164 may be radially and/or rotationally adjustable.

The stereoscopic camera 12 of FIG. 3 may include one or more optical filters 168 to selectively transmit desired wavelengths of light. Each of the optical paths may have a separate filter. The inclusion of separate filters enables, for example, different wavelengths of light to be filtered from the left and right optical paths at the same time, which enables, for example, fluorescent images to be displayed in conjunction with visible light images.

Referring to FIG. 3, the filter 168 may include a wheel that is rotatable about an axis of rotation and capable of accommodating multiple different optical filter pairs. The lenses of the optical assembly 102, the front lens set 158, the zoom lens assembly 160, and the lens barrel set 166 may be configured to pass a relatively wide bandwidth of light including wavelengths of interest to an operator and undesirable wavelengths. In other embodiments, the filter 168 may include a digital micro-mirror, which can change a light path's direction at video frame rates.

Referring to FIG. 3, the stereoscopic camera 12 may include a final optical element set 170 for focusing light received from the filter 168 onto an optical image sensor 172, which may be connected to a flexible member 174. The final optical element set 170 may include right and left positive converging lenses which are adjustable radially and/or axially to correct magnification and/or focusing aberrations in the right and left optical paths prior to the light reaching the optical image sensor 172.

Referring to FIG. 3, the optical image sensor 172 is configured to acquire and/or record incident light that is received from the final optical element set 170. The optical image sensor 172 may include separate right and left optical image sensors for the right and left optical paths and may include, but are not limited to, complementary metal-oxide-semiconductor ("CMOS") sensing elements, N-type metal-oxide-semiconductor ("NMOS"), and/or semiconductor charge-coupled device ("CCD") sensing elements. The controller C may be configured to measure and calculate camera model parameters for each value of magnification and working distance. To match the left and right stereoscopic view of a target site 16, the output of the stereoscopic camera 12 may be calibrated using a mathematical model executable by the controller C.

II. Disparity Mode

Figure 4:
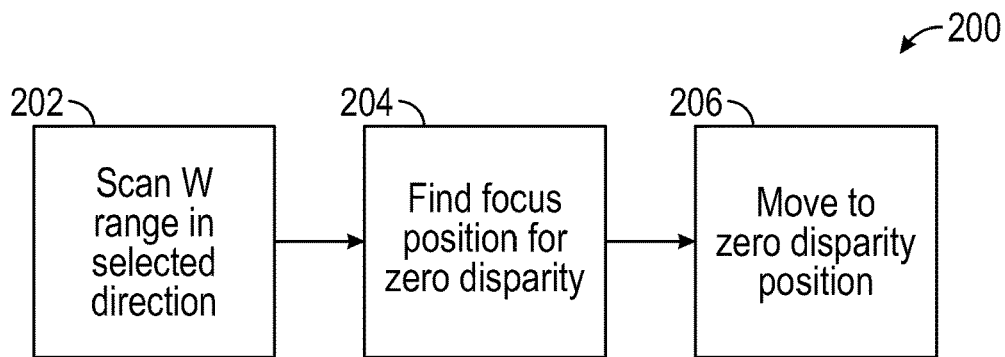
FIG. 4 is a flowchart of an example method executable by the controller of FIG. 1, implementing a disparity mode for autofocusing.

Referring now to FIG. 4, a flowchart of method 200 is shown. Method 200 is an example implementation of the disparity mode 50 of FIG. 1 and may be embodied as computer-readable code or instructions stored on and partially executable by the controller C of FIG. 1. Method 200 need not be applied in the specific order recited herein and may be dynamically executed. Furthermore, it is to be understood that some steps may be eliminated. As used herein, the terms 'dynamic' and 'dynamically' describe steps or processes that are executed in real-time and are characterized by monitoring or otherwise determining states of parameters and regularly or periodically updating the states of the parameters during execution of a routine or between iterations of execution of the routine.

Figure 5A:
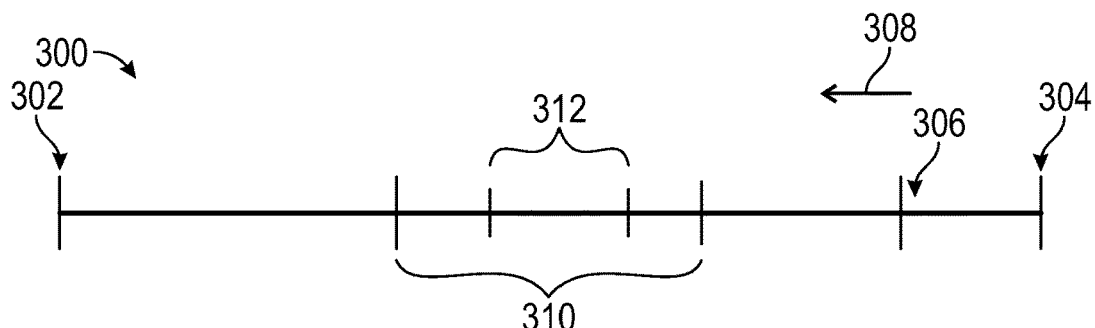
FIG. 5A is a schematic diagram of a distance scale showing a valid disparity region and a valid sharpness region, for an example stereoscopic camera.
Figure 5B:
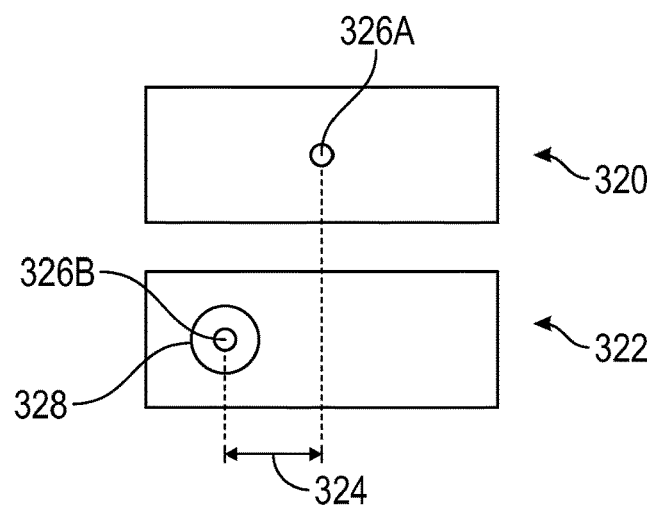
FIG. 5B is a schematic diagram illustrating disparity for an example left image and right image.

Given a 3D stereoscopic imaging device (e.g., a stereoscopic microscope) with a variable working distance, the challenge is to figure out how to change the working distance W quickly (e.g., by adjusting the focus motor 110) and automatically get an image in focus, regardless of the initial state of the working distance W. The first challenge is obtaining a feedback signal to use to change the working distance W. In the disparity mode 50, the feedback signal used is a disparity signal. A schematic diagram illustrating disparity for an example left image 320 and right image 322 is shown in FIG. 5B, which is not drawn to scale. The disparity value/signal 324 may be defined as the numerical pixel offset between an identifiable region 326A in the left eye image 320 and the same identifiable region 326B in the right eye image 322. Referring to FIG. 5B, the disparity signal may be calculated by taking the identifiable region 326A of the left eye image 320 and performing a template match over a second (larger) region 328 containing the same coordinates of the identifiable region 326B in the right eye image 322. The second region 328 is larger than the identifiable region 326A/326B. A second challenge is searching across the entire working distance W, since the initial state of the working distance W may result in a completely blurry image, making the disparity signal unreliable. A search must therefore be performed, and the focus motor 110 moved into a region where the disparity signal is valid and can be used in a feedback controller.

Referring to FIG. 4, method 200 begins at block 202, where the controller C is programmed to examine the state of the robotic arm 24 and determine a selected direction 308 (see FIG. 5A) in which the focus motor 110 needs to move to get the image into focus. Referring to FIG. 5A, a distance scale 300 is shown, between a minimum working distance 302 and a maximum working distance 304. The initial state of the working distance W (and corresponding initial position of the focus motor 110 of FIG. 2) is indicated by starting point 306. The selected direction 308 matches the direction of movement of the robotic arm 24. The data is examined to determine which direction the robotic arm 24 has moved since the last time that the image was in focus. Searching in this direction enables a valid disparity region 310 (see FIG. 5A) to be encountered rapidly. FIG. 5A shows the valid disparity region 310 and a valid sharpness region 312. The valid sharpness region 312 is smaller than and contained within the valid disparity region 310.

Also, per block 202 of FIG. 4, the controller C is programmed to scan or sweep the range of the working distance (W) in the selected direction 308 and calculate the disparity signal at each step. As noted above, referring to FIG. 5B, the disparity signal 324 may be calculated by taking the identifiable region 326A of the left eye image 320 and performing a template match over a larger second region 328 containing the same coordinates of the identifiable region 326B in the right eye image 322. A pixel offset is obtained by calculating the location of the optimal template match, the pixel offset being set as the disparity signal. Other methods may be employed.

Figure 6:
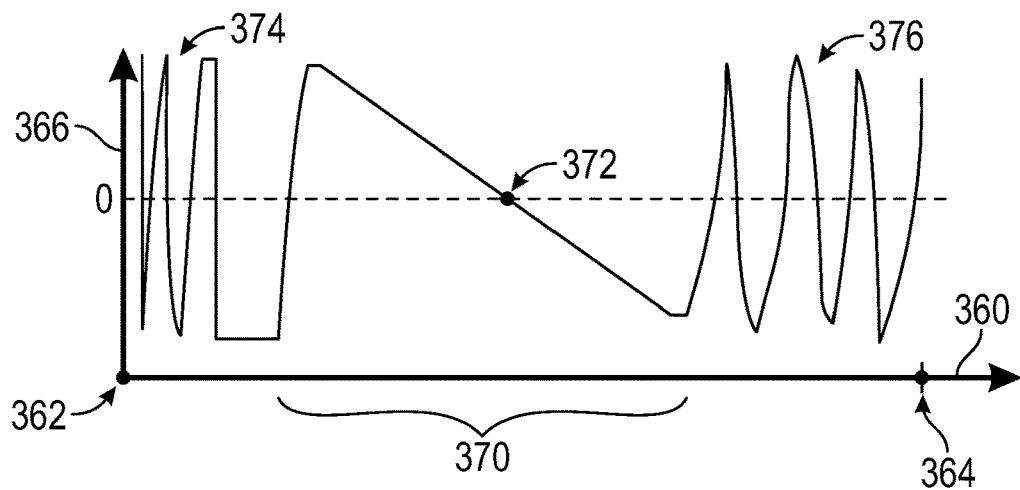
FIG. 6 is a schematic graph illustrating a disparity signal relative to a variable working distance, for an example stereoscopic camera.

Referring to FIG. 6, a schematic graph of an example disparity signal is shown. A horizontal axis 360 indicates working distance, between a minimum working distance 362 and a maximum working distance 364. A vertical axis 366 indicates the magnitude of the disparity signal. Referring to FIG. 6, as the image becomes more and more in focus, the disparity signal trends linearly towards zero (at zero-disparity position 372) from the ends of the valid disparity region 370. The zero-disparity position 372 indicates a disparity signal of zero. When the disparity signal is zero, the left and right images overlap and are not offset, resulting in an image that is in better focus. Referring to FIG. 6, the disparity signal within a valid disparity region 370 reflects valid/legitimate values, while the disparity signal values in a first outer region 374 and a second outer region 376 reflect artifacts or nonsensical values. The artifacts are an outcome of the way that the disparity signal is calculated, for example, with the template matching process described above. As one moves further away from the zero-disparity position 372, the image becomes increasingly blurry, until eventually the image is almost completely blurred at which point the pixel offset obtained by calculating the location of the optimal template match is simply returning noise. Once a region of variable working distance is entered where numerically valid disparity is detected (e.g., the valid disparity region 310 in FIG. 5A), the controller C is programmed to switch to using a feedback controller (e.g., a PID controller) to move the focus motor 110 accordingly and drive the disparity to zero.

Per block 204 of FIG. 4, the controller C is programmed to determine motor commands for the focus motor 110 where the calculated disparity signal is zero. This may be done via a closed-loop control module configured to obtain an error value (E) as a difference between the desired disparity ($D_{desired}=0$) and the estimated disparity ($D_{estimated}$).

$$E=[{}^{LIM}D_{estimated}-D_{desired}]$$

The closed-loop control module may be embedded in the controller C or otherwise accessible to the controller C. The closed-loop control module is configured to minimize the error value over time by adjusting a control variable (working distance in this case) to a new value. The closed-loop control module may be a proportional-derivative (PD) control module or a proportional-integral (PI) control module or a proportional-integral-derivative (PID) control module. As understood by those skilled in the art, a PI control module and PID control module employs a feedback loop continuously calculating an error value, the error value being the difference between a desired value and a measured process variable. The PI control module applies a correction based on proportional and integral terms, while the PID control module further includes a derivative term and the PD control module applies a correction based on proportional and derivative terms.

Per block 206 of FIG. 4, the controller C is programmed to move the focus motor 110 to the corresponding zero-disparity position 372 (as determined in block 204) to obtain an in-focus image. This is not a straightforward matter as the "perfect focus disparity" has been observed to be highly variable from unit to unit. Additionally, changes such as the stereoscopic camera 12 heating up can shift the zero-disparity position 372. The disparity mode 50 provides a single function call, when the robotic arm 24 is not moving, to get the image in focus from any initial condition at any time. Another technical advantage is that since there are two images available in the stereoscopic camera 12, no additional hardware is required to measure absolute distance to the ground, thus eliminating the need for a range finder.

III. Sharpness and Disparity Based Autofocus

Figure 7:
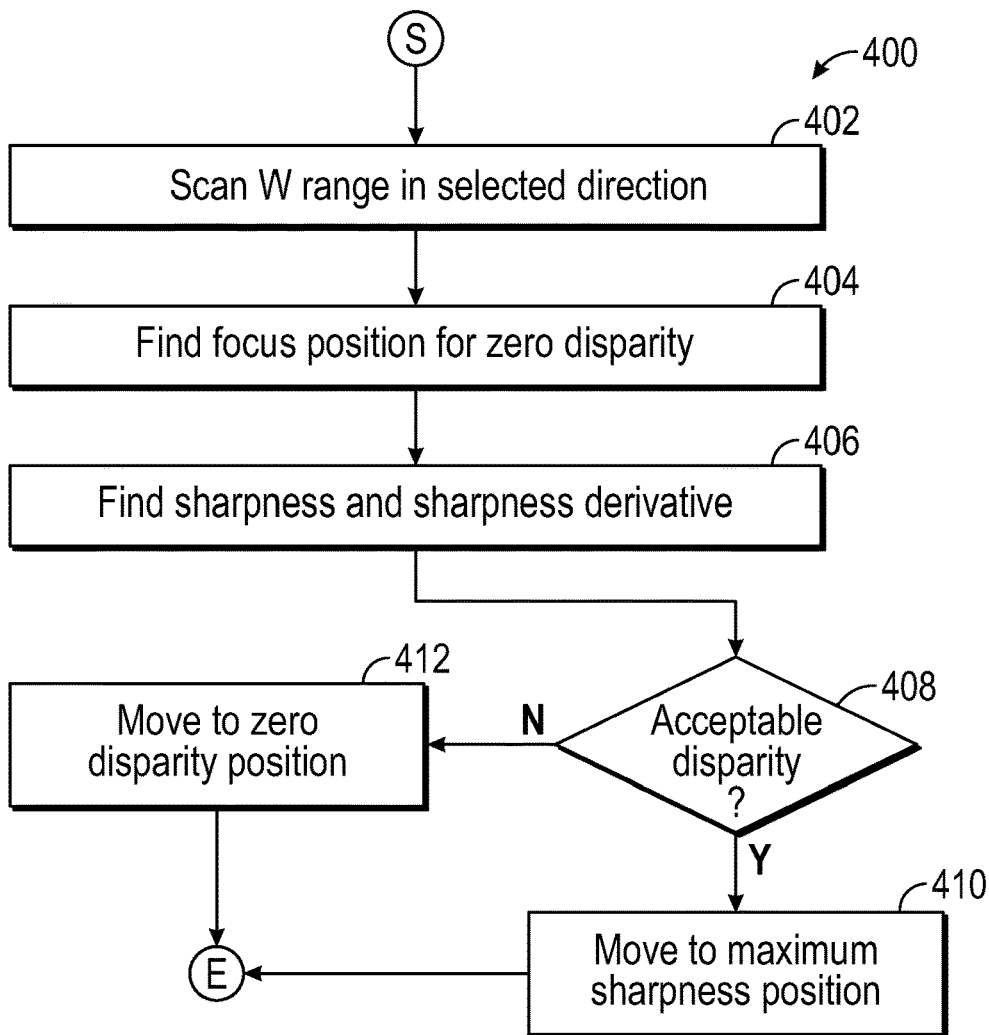
FIG. 7 is a flowchart of an example method executable by the controller of FIG. 1, implementing a sharpness control mode for autofocusing.

Referring now to FIG. 7, a flowchart of the method 400 is shown. Method 400 is an example implementation of the sharpness control mode 52 of FIG. 1 and may be embodied as computer-readable code or instructions stored on and partially executable by the controller C of FIG. 1. Method 400 need not be applied in the specific order recited herein and may be dynamically executed. Furthermore, it is to be understood that some steps may be eliminated. The sharpness control mode 52 improves the overall image when the stereoscopic camera 12 is in focus and reduces poor image quality due to disparity variance. In many circumstances, the position of maximum sharpness is offset from the position of zero disparity. The challenge here is to apply a dynamic adjustment to converge to the location of maximum sharpness. Another challenge is the validity of the sharpness signal across the working distance range, since the portions outside of the valid sharpness region 312 (see FIG. 5A) are unusable/blurry. As shown in FIG. 5A, the valid sharpness region 312 is relatively small, particularly at high magnification.

Figure 8A:
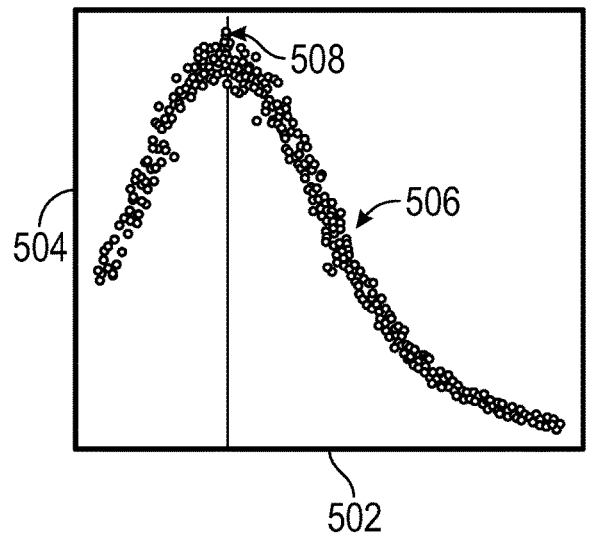
FIGS. 8A and 8B are schematic graphs showing examples of sharpness signal values (relative to focus motor position) for different magnification values, for an example stereoscopic camera.
Figure 8B:
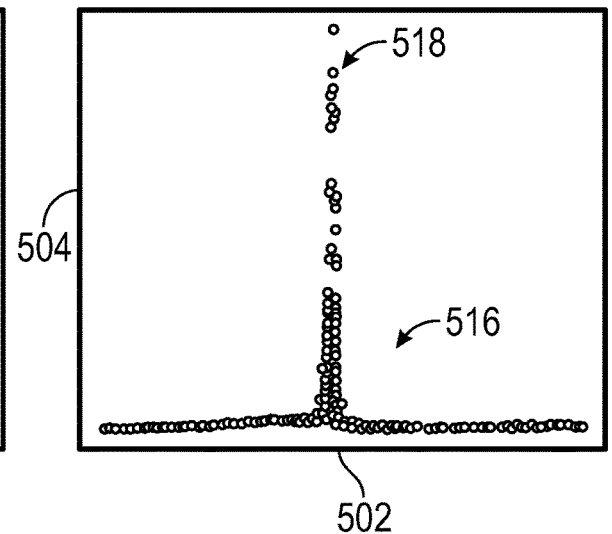

FIGS. 8A and 8B are schematic graphs showing examples of sharpness signal values relative to various positions of the focus motor 110, for an example stereoscopic camera 12. In FIGS. 8A and 8B, the horizontal axis 502 reflects focus motor position while the vertical axis 504 reflects sharpness signal amplitude. Trace 506 in FIG. 8A illustrates a sharpness signal obtained at a magnification of 1×, the sharpness signal having a maximum value at motor position 508. Trace 516 in FIG. 8B illustrates a sharpness signal obtained at a magnification of 10X, the sharpness signal having a maximum value at motor position 518. The breadth of the sharpness signal varies with the magnification or zoom. As shown in FIGS. 8A and 8B, the breadth is narrower at regions of higher magnification.

Method 400 of FIG. 7 begins with block 402, where the controller C is programmed to determine a selected direction (e.g., selected direction 308 in FIG. 5A) in which the focus motor 110 needs to move to get into focus. The selected direction is set to be the direction that the robotic arm 24 had moved at the last time that the image was in focus. The controller C is programmed to scan the range of the working distance (W) in the selected direction 308.

Per block 404 of FIG. 7, the controller C is programmed to determine the motor commands for the focus motor 110 where the calculated disparity signal is zero (see for example, the zero-disparity position 372 in FIG. 6). This may be done via a closed-loop control module configured to obtain an error value (E) as a difference between the desired disparity ($D_{desired}=0$) and the estimated disparity ($D_{estimated}$).

$$E=[{}^{LM}D_{estimated}-D_{desired}]$$

The closed-loop control module may be embedded in the controller C or otherwise accessible to the controller C. The closed-loop control module is configured to minimize the error value over time by adjusting a control variable (working distance in this case) to a new value. The closed-loop control module may be a proportional-derivative (PD) control module or a proportional-integral (PI) control module or a proportional-integral-derivative (PID) control module. As understood by those skilled in the art, a PI control module and PID control module employs a feedback loop continuously calculating an error value, the error value being the difference between a desired value and a measured process variable. The PI control module applies a correction based on proportional and integral terms, while the PID control module further includes a derivative term and the PD control module applies a correction based on proportional and derivative terms.

Figure 8C:
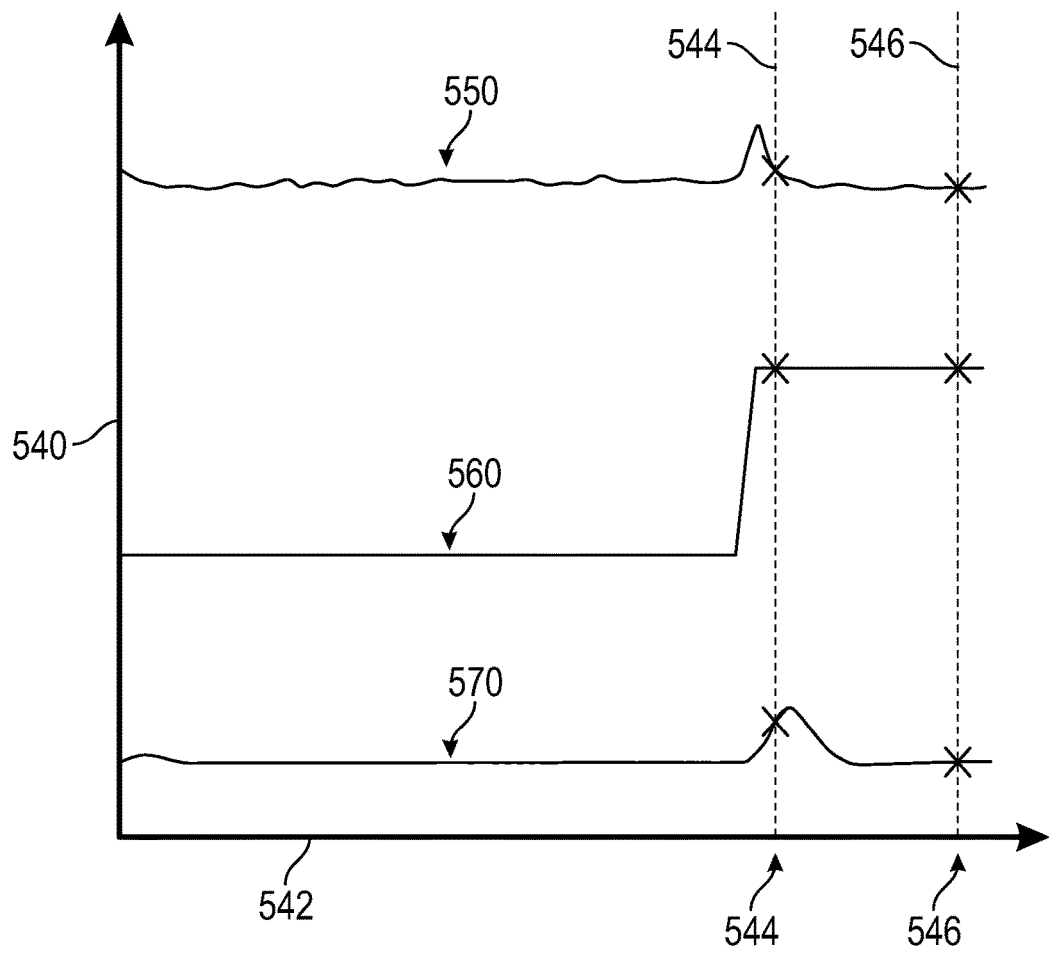
FIG. 8C is a schematic diagram illustrating sharpness, maximum sharpness, and derivative of maximum sharpness (relative to focus motor position) for an example stereoscopic camera.

Per block 406 of FIG. 7, the controller C is programmed to determine or track multiple of sharpness parameters, including a sharpness signal, a maximum sharpness signal and a derivative of the maximum sharpness, i.e., rate of change over time of the maximum sharpness. FIG. 8C is a schematic diagram illustrating examples of a sharpness signal 550, a maximum sharpness signal 560, and a derivative 570 of maximum sharpness for an example stereoscopic camera 12. The vertical axis 540 indicates the magnitude of the respective sharpness parameter while the horizontal axis 542 indicates the corresponding position of the focus motor 110. The sharpness parameters reflect the crispness of an image. The sharpness signal 550 may be defined as the contrast between the edges of an object in an image, which are high frequency components of the image. The sharpness signal 550 may be calculated by calculating the variance of the Laplacian of a Gaussian Blur of each image frame of the stereoscopic image. As understood by those skilled in the art, the Laplacian (sometimes referred to as a Laplace operator) is a differential operator given by the divergence of the gradient of a function on Euclidean space. A Gaussian blur may be obtained by blurring or smoothing an image using a Gaussian function. These calculations may be performed using mathematical software, machine learning algorithms, and processing devices available to those skilled in the art. The definition of the sharpness signal 550 may be varied based on the application at hand.

Referring to FIG. 8C, the maximum sharpness signal 560 may be defined as the highest sharpness value observed during the scan time. The maximum sharpness signal 560 is continually updated, and the derivative 570 of maximum sharpness is calculated with respect to time. In some embodiments, the derivative 570 ($dS_{max}/dt$) of maximum sharpness may be obtained as: $dS_{max}/dt=\text{filter}([\Delta s[n+1]-\Delta s[n]]/T_s)$, where $T_s$ is the sample rate, n is the sample count, $\Delta s$ is the change in maximum sharpness and the filter function may be a smoothing or noise-reduction filter function available to those skilled in the art. The sharpness signal 550 may come in at a different rate in a different thread and may be calculated at slightly different times than when the focus motor command is updated.

As shown in FIG. 8C, the derivative 570 of the maximum sharpness reaches a maximum at first position 544. When the derivative 570 of the maximum sharpness goes back to zero, this means that the best sharpness location has passed, and the controller C is triggered. For example, the controller C may be triggered at the second position 546, when the derivative 570 has settled at zero for a predefined number of steps. The controller C is programmed to command the focus motor 110 back to the first position 544, which is deemed the maximum sharpness position.

The method 400 of FIG. 7 proceeds from block 406 to block 408. Per block 408 of FIG. 7, the controller C is programmed to determine if the disparity signal is at or below an acceptable threshold at the maximum sharpness position. If so, the method 400 proceeds to block 410, where the focus motor 110 is commanded to the working distance position corresponding to maximum sharpness (obtained in block 406). By leveraging the disparity signal to guarantee convergence to the small sharpness region, method 400 is fast, robust, and works well at multiple zoom levels. By maximizing sharpness, the resulting image is less blurry than simply converging to disparity alone.

If disparity signal is above the acceptable threshold, the method 400 proceeds to block 412 where the focus motor 110 is commanded to the zero-disparity position 372 (see FIG. 6), obtained in block 404. In some cases where the stereoscopic camera 12 is improperly calibrated, the location corresponding to maximum sharpness may result in unacceptable high disparity, which makes it difficult to perceive in three dimensions. In this case, since maximum sharpness cannot be used, and the method 400 returns to the location of zero disparity. Using sharpness alone is challenging at high magnification due to the extremely small region with meaningful sharpness information.

In summary, the method 400 performs multiple sweeps, uses disparity feedback, and sharpness feedback to change the working distance W to achieve optimal focus. When considering an image, the image may be considered maximally in focus if the disparity is not too large and the sharpness of the image is maximized. The sharpness control mode 52 enables optimal convergence to maximum sharpness by pairing sharpness parameters with the disparity signal, which has a valid disparity region 310 (see FIG. 5A) that is larger and contains the valid sharpness region 312 (see FIG. 5A).

IV. Target Locking Mode

Figure 9:
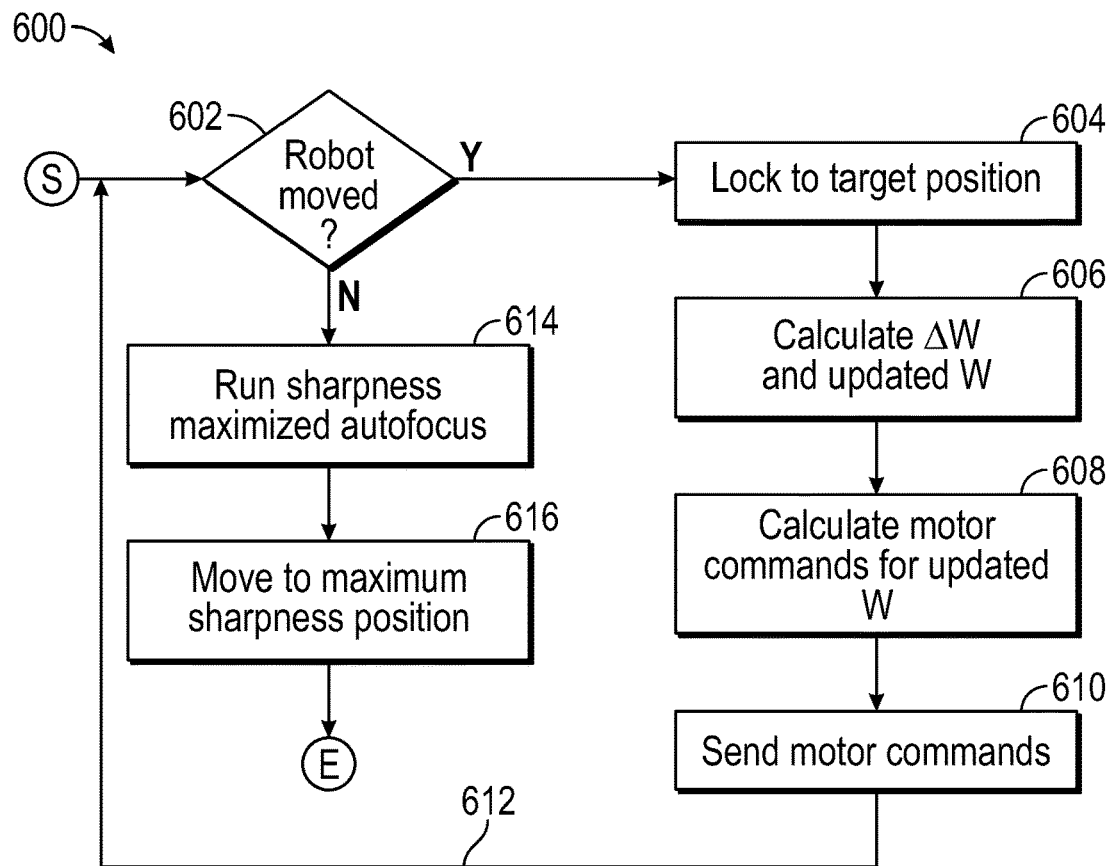
FIG. 9 is a flowchart of an example method executable by the controller of FIG. 1, implementing a target locking mode for autofocusing.

Referring now to FIG. 9, a flowchart of an example method 600 is shown. Method 600 is an example implementation of the target locking mode 54 of FIG. 1 and may be embodied as computer-readable code or instructions stored on and partially executable by the controller C of FIG. 1. Method 600 need not be applied in the specific order recited herein and may be dynamically executed. Furthermore, it is to be understood that some steps may be eliminated.

In some embodiments, referring to FIG. 1, the target locking mode 54 begins when an operator selects target locking mode 54 (e.g., via an input device 66 such as a mouse), which causes an instruction message or signal to be transmitted to the controller C and/or the robotic arm controller 42. When an instruction is received, the example controller C and/or the robotic arm controller 42 may record the current working distance, magnification, focus, and/or other optical parameters of the stereoscopic camera 12. The current position of the target site 16 may be determined from position data of the various joints of the robotic arm 24. The controller C and/or the robotic arm controller 42 may also record a current image of the target site 16.

The target locking mode 54 enables the stereoscopic camera 12 to be moved around anywhere in 3D space (via the robotic arm 24), permitting changes in working distance, while keeping the target site 16 locked and in focus in real-time. A challenge of keeping the image in focus during movement of the robotic arm 24 occurs where the orientation of the stereoscopic camera 12 changes, i.e., the direction of the view vector 118 (see FIG. 3) of the stereoscopic camera 12 in 3D space. In these embodiments, the target locking mode 54 enables the robotic arm 24 to operate as an extension of a surgeon by enabling the stereoscopic camera 12 to be re-oriented while being locked onto a specific point (e.g., target point 120 shown in FIG. 3) on the target site 16.

Figure 10:
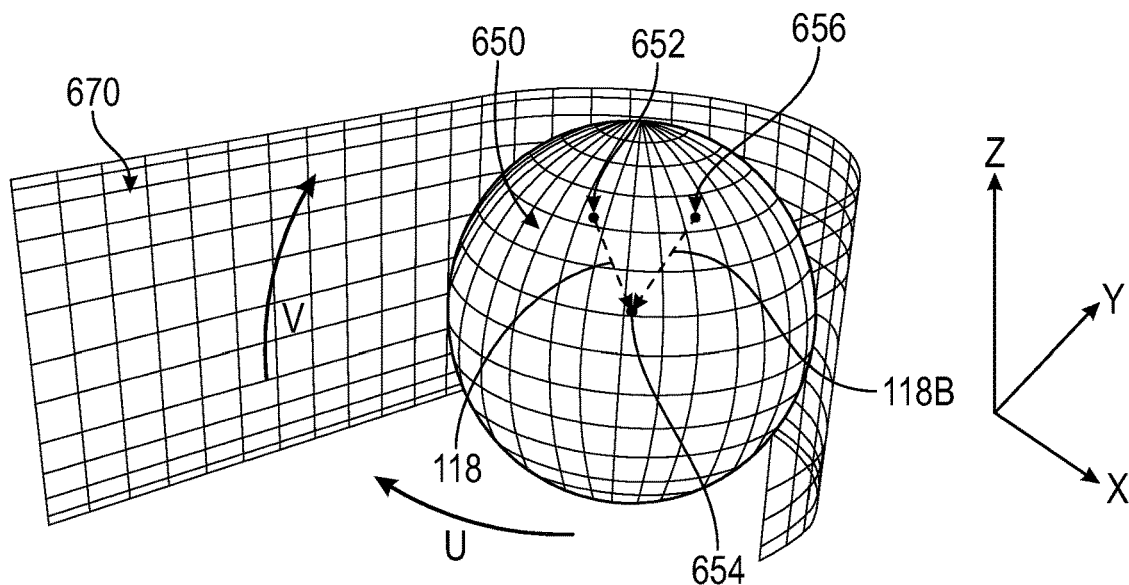
FIG. 10 is a schematic diagram of an example virtual sphere employable in the third method of FIG. 9.

Method 600 begins with block 602 of FIG. 9, where the controller C is programmed to determine if the robotic arm 24 has moved. If so, the method 600 proceeds from block 602 to block 604 where the position of the target site 16 is locked via a target-lock function. The target-lock function restricts the position of the stereoscopic camera 12 to the outer surface of a virtual sphere, for example, outer surface 652 of a virtual sphere 650 shown in FIG. 10, based on the current position of the target site 16. FIG. 10 is a schematic diagram of an example virtual sphere 650 employable in the method 600. Referring to FIG. 10, a given point on the outer surface 652 may be given by an equation that is a function of rotational sphere angles V and U.

Referring to FIG. 10, the view vector 118 (shown also in FIG. 3) of the stereoscopic camera 12 points to the center 654 of the virtual sphere 650. The center 654 has the same coordinates in XYZ space as a selected point in the target site 16, such as target point 120 shown in FIG. 3. Referring to FIG. 10, an end location 656 (of the stereoscopic camera 12) on the outer surface 652 may be obtained differently, based on the type of input received. In some embodiments, input is received via an input device 66 (e.g., a joystick or mouse) as shown in FIG. 1. The controller C and/or the robotic arm controller 42 may be adapted to convert 'up', 'down', 'left', and 'right' from camera coordinates to robotic base frame coordinates, which are provided as X and Y vectors. The X and Y vectors are used by the controller C and/or the robotic arm controller 42 for directly determining how the stereoscopic camera 12 is to move on the virtual sphere 650 to determine the end location 656.

In some examples, the controller C is configured to receive orbit input data, expressed in the form of rotational angles. In these examples, referring to FIG. 10, the controller C holds the first sphere angle V constant while iterating movement along the second sphere angle U of the virtual sphere 650. The iterative movement along the second sphere angle U enables the end location 656 to be determined for an orbit input. In some embodiments, the virtual sphere 650 may be represented by a different shape and the outer surface 652 may be represented by a planar surface 670.

After the end location 656 is determined, the controller C is configured to calculate an amount of rotation needed for the stereoscopic camera 12 to maintain the lock at the XYZ coordinates of the selected point after the stereoscopic camera 12 has been moved. The controller C (and/or the robotic arm controller 42) may determine roll and pitch amounts for the stereoscopic camera 12 and provide anti-yaw correction. The example controller C and/or the robotic arm controller 42 of FIG. 1 enable an operator to move the stereoscopic camera 12 over the outer surface 652 to end location 656, while keeping the stereoscopic camera 12 pointed at the center 654 (as indicated by view vector 118B) of the virtual sphere 650, thereby keeping the target site 16 in focus during the movement. In other words, the controller C is configured to determine how the stereoscopic camera 12 is to be orientated given its new position on the virtual sphere 650 such that the view vector 118B of the end location 656 is provided at the same XYZ coordinates at the center of the virtual sphere 650 (corresponding to the selected point). Additionally, the controller C and/or the robotic arm controller 42 are adapted to determine the joint angles of the robotic arm 24 and/or the coupling plate 26 needed to achieve the desired orientation.

The method 600 proceeds from block 604 to block 606, where the controller C is programmed to calculate the change in working distance (ΔW) relative to the previously saved value (or previous iteration), due to the movement of the stereoscopic camera 12 via the robotic arm 24. The controller C is programmed to obtain an updated value of the working distance (W). In other words, displacement of the working distance (W) due to robotic movement is tracked every movement cycle.

The method 600 proceeds from block 606 to block 608, where the controller C is programmed to calculate motor commands for the focus motor 110 corresponding to the updated value of the working distance (W). In some embodiments, a calibrated look-up-table is employed to convert the change in working distance to commands for the focus motor 110. The method 600 proceeds to block 610. Per block 610 of FIG. 9, the controller C is programmed to send the calculated motor commands from block 608 to move the focus motor 110 such that the image does not go out of focus as the working distance (W) is being updated in each iteration.

If motion of the robotic arm 24 is no longer detected per block 602, the method 600 proceeds to block 614 where the sharpness maximized position is located. Similar to block 406 of FIG. 7, in block 614, the controller C is programmed to determine or track multiple sharpness parameters, including a sharpness signal, a maximum sharpness signal and a derivative of the maximum sharpness, i.e., rate of change over time. FIG. 8C shows examples of a sharpness signal 550, a maximum sharpness signal 560, and a derivative 570 of maximum sharpness for an example stereoscopic camera 12. The vertical axis 540 indicates the magnitude of the respective sharpness parameter while the horizontal axis 542 indicates the corresponding position of the focus motor 110. As noted previously, the sharpness signal 550 may be calculated by calculating the variance of the Laplacian of a Gaussian Blur of each image frame. The definition of the sharpness signal 550 may be varied based on the application at hand. The maximum sharpness signal 560 may be defined as the largest sharpness value observed during the scan time. The maximum sharpness signal 560 is continually updated, and the derivative 570 of maximum sharpness is calculated over time. As shown in FIG. 8C, the derivative 570 of the maximum sharpness reaches a maximum at first position 544. When the derivative 570 of the maximum sharpness goes back to zero, this means that the best sharpness location has passed, and the controller C is triggered. For example, the controller C may be triggered at the second position 546, when the derivative 570 has settled at zero for a predefined number of steps. The first position 544 is deemed the maximum sharpness position.

From block 614, the method 600 of FIG. 9 proceeds to block 616, where the controller C is adapted to move the focus motor 110 to the maximum sharpness position. As indicated by line 612, the method 600 loops back to block 602 from block 610. Every update cycle, the method 600 updates the amount of displacement moved along the working distance (W), e.g., in meters. This movement amount is then converged to motor focus commands using a calibrated look-up-table. This motor command is then sent, resulting in the image not going out of focus as the working distance (W) is changed. The radius of the virtual sphere 650 in each iteration is reset to be the updated value of the working distance (W), with internal target-lock function calculations updating the radius of the virtual sphere 650 each cycle. If the target site 16 is moving, the selected point (at the center 654 of the virtual sphere 650) is replaced with a dynamic trajectory that corresponds to the motion of the target site 16.

In summary, the method 600 enables focus to be maintained while the robotic arm 24 is being moved in three-dimensional space while looking at a target site 16. The controller C dynamically interprets movement of the robotic arm 24 and calculates how far to move to maintain focus. At the end of all movement of the robotic arm 24, the focus motor 110 is moved to the location of maximum sharpness. The amount of this adjustment (moving to the location of maximum sharpness) may be small, due to continuous tracking during operation of the robotic arm 24. This results in an image that always appears in focus, even if the robotic arm 24 is changing the working distance. Referring to FIG. 1, in the target locking mode 54, changes in working distance W (because of movement of the robotic arm 24) are permitted. The allowable change in working distance W may be limited such that the radius of the virtual sphere 650 does not exceed the maximum and minimum working distance permitted by the hardware. In some embodiments, a feature flag may be inserted to enforce artificial robot boundaries to prevent the robotic arm 24 from exceeding these limitations on the working distance W.

In some embodiments, the controller C may program and store a path of motion within a visualization of an object, made from different viewing angles. For example, the controller C and/or the robotic arm controller 42 may be programmed to perform an ophthalmological examination of a patient's eye by pivoting about a point inside the eye. In this example, the robotic arm 24 sweeps the stereoscopic camera 12 in a generally conical motion such that the patient's eye is viewed from a plethora of viewing angles. Such motion of surgical site visualizations may be used to select the best angle to preclude spurious reflections from illumination or to see around obstructions in alternative viewing angles.

V. Continuous Autofocus Mode

Figure 11:
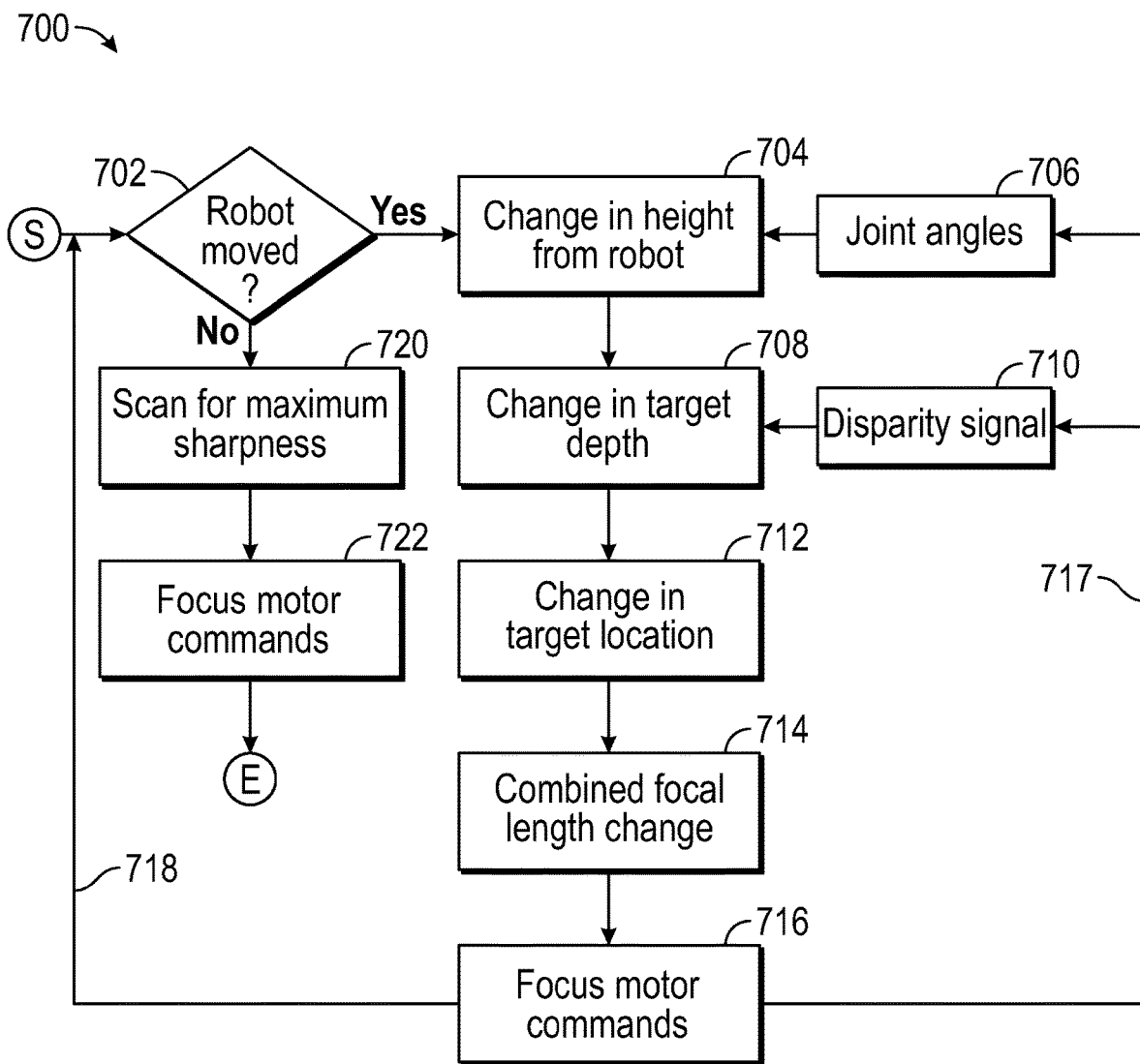
FIG. 11 is a flowchart of an example method executable by the controller of FIG. 1, implementing a continuous autofocusing mode for autofocusing.

Referring now to FIG. 11, a flowchart of a method 700 is shown. Method 700 is an example implementation of the continuous autofocus mode 56 of FIG. 1 and may be embodied as computer-readable code or instructions stored on and partially executable by the controller C of FIG. 1. Method 700 need not be applied in the specific order recited herein and may be dynamically executed. Furthermore, it is to be understood that some steps may be eliminated.

The continuous autofocus mode 56 of FIG. 1 is adapted to keep an image in focus as the robotic arm 24 moves, independent of movement type, and provide smooth, low-noise maximum sharpness adjustments at the end of the move. This means the image remains in focus, even if the stereoscopic camera 12 is rotating to view different scenes, the scene itself is changing depth, the working distance W is changing, or all of the above at the same time. As described below, the continuous autofocus mode 56 measures relative changes of the view vector 118 (see FIG. 2) by measuring the current state of the robotic arm 24 as well as relative changes of the target depth (i.e., position in the axial direction, Z axis here) by using dynamic control of the disparity signal. This enables initialization at a point that the image is detected in focus (either automatically or by the user), and after this point the image remains in focus. Because the disparity signal is used dynamically during movement, changes in depth (i.e., position in the axial direction) that occur when the robotic arm 24 moves will stay in focus.

Method 700 begins with block 702 of FIG. 11, the controller C is programmed to determine if the robotic arm 24 has moved. If so, the method 700 proceeds to block 704, where the controller C is programmed to determine a change in height due to movement of the robotic arm 24 (detected in block 702). The height is defined as the change in position of the stereoscopic camera 12 along the axial direction (Z axis here) from movement of the robotic arm 24. The controller C may calculate the change in height using position data of the joints (e.g., joint sensor 33 of FIG. 1) and other parts of the robotic arm 24, as indicated by block 706.

The method 700 of FIG. 11 proceeds from block 704 to block 708, where the controller C is programmed to determine a change in target depth ($\Delta Z\_target$). As indicated by block 710, the controller C may receive input data pertaining to the disparity signal in order to calculate the change in target depth. The change in target depth ($\Delta Z\_target$) may be calculated using feedback control with a closed-loop control module, which may be a PI controller, a PD controller and/or a PID controller. In one example, the change in target depth ($\Delta Z\_target$) is calculated using a PID controller and disparity values as follows:

$$\Delta Z\_target = Kp(Rc-Rt) + Ki\int(Rc-Rt)dt - Kd*dRc/dt$$

Here, Rc is the current disparity value, and Rt is the initial target disparity value, defined as the disparity value recorded when the starting values were initialized and stored. Here, Kp, Ki and Kd are the proportional, integral and derivative constants, respectively, from the PID controller, with the process variable being a difference between the current disparity value (Rc) and the initial target disparity (Rt). The constants Kp, Ki and Kd may be obtained via calibration with known changes in target depth (changes along Z axis here).

The method 700 of FIG. 11 proceeds from block 708 to block 712, where the controller C is programmed to determine a change in location coordinates of the target site 16 based on the change in target depth (from block 708). The stored location of the Z component of the target site 16 is updated as:

$$Z\_updated = Z\_initial - \Delta Z\_target$$

The method 700 then proceeds to block 714, where the controller C is programmed to determine a combined focal length change ($\Delta F$) and update the focal length (F). At each update cycle, the focal length F is updated using a feed-forward term from the robotic arm 24 plus a feedback term from the target depth disparity, as shown below:

$$\Delta F = \Delta F\_robot + \Delta F\_target$$

The focal length F is updated by two elements: firstly, by how much the terminating point of the view vector 118 of the stereoscopic camera 12 has changed, and secondly by how much the target depth of the target 16 has changed.

Because the two elements are in different frames of reference, a homogenous transformation matrix (4×4) is employed to transform base coordinates (Xbase, Ybase, Zbase) in a robotic base frame to a camera coordinate frame. The base coordinates (Xbase, Ybase, Zbase) represent the instant or current location of the target site 16 in a robotic base frame. The homogenous transformation matrix is composed of a rotation matrix Q (3×3) and translation vector P and may be represented as:

$$\begin{bmatrix} Q & P \\ 0 & 1 \end{bmatrix}.$$

The rotation matrix Q has 3 by 3 components and the translation vector P has 3 by 1 components. The translation vector P represents the offset (x0, y0, z0) from the robotic base frame to the camera frame, where the origin of the robotic base frame is zero (0, 0, 0) and the origin of the camera frame in the robotic base frame is (x0, y0, z0). The equation below converts the base coordinates (in the robotic base frame) to the camera frame.

$$\begin{bmatrix} Xbase \\ Ybase \\ Zbase \\ 1 \end{bmatrix} = \begin{bmatrix} Q & P \\ 0 & 1 \end{bmatrix} \begin{bmatrix} 0 \\ 0 \\ F \\ 1 \end{bmatrix}, \quad (eq.\ 1)$$

$$\text{where } P = \begin{bmatrix} x0 \\ y0 \\ z0 \\ 1 \end{bmatrix} \text{ and } Q = \begin{bmatrix} x1 & x2 & x3 \\ y1 & y2 & y3 \\ z1 & z2 & z3 \end{bmatrix}.$$

Expanding this equation results in:

$$\begin{bmatrix} Xbase \\ Ybase \\ Zbase \\ 1 \end{bmatrix} = F\begin{bmatrix} x3 \\ y3 \\ z3 \\ 1 \end{bmatrix} + \begin{bmatrix} x0 \\ y0 \\ z0 \\ 1 \end{bmatrix} \quad (eq.\ 2)$$

Here the vector (x3, y3, z3) represents the third column of the rotational matrix Q, which is the Z basis vector of the rotational space of the transformation matrix. The z position component of the Z basis vector is represented by z3. The updated focal length F may be calculated using the following equations:

$$Zbase = F(z3) + z0 \quad (eq.\ 3)$$

$$F = \left(\frac{Zbase - z0}{z3}\right) \quad (eq.\ 4)$$

The method 700 proceeds from block 714 to block 716. Per block 716, the controller C is configured to calculate the motor commands corresponding to the updated focal length F determined in block 714. The motor commands are transmitted and the focus motor 110 is moved the correct amount, determined through calibration, such that the working distance W is the same as the updated focal length F. Referring to FIG. 11, as indicated by line 717, the updated focal length F (and updated working distance W) may be fed back into block 706 in order to update data pertaining to the joint angles of the robotic arm 24. As noted above, the data on joint angles is used in block 704 to obtain a change in height due to movement of the robotic arm 24. Additionally, as shown by line 717, the updated focal length F may be inputted into block 710 in order to update the disparity signal information used to obtain the change in target depth in block 708. Finally, the method 700 loops back to block 702 from block 716, as indicated by line 718 in FIG. 11.

Referring back to block 702 of FIG. 11, if no movement of the robotic arm 24 is detected, the method 700 proceeds from block 702 to block 720, where the controller C is programmed to scan and calculate the focus motor position for maximum sharpness. Similar to block 406 of FIG. 7, in block 614, the controller C is programmed to determine or track multiple of sharpness parameters, including a sharpness signal, a maximum sharpness signal and a derivative of the maximum sharpness, i.e., rate of change over time. FIG. 8C shows examples of a sharpness signal 550, a maximum sharpness signal 560, and a derivative 570 of maximum sharpness for an example stereoscopic camera 12. The vertical axis 540 indicate the magnitude of the respective sharpness parameter while the horizontal axis 542 indicates the corresponding position of the focus motor 110. As noted previously, the sharpness signal 550 may be calculated by calculating the variance of the Laplacian of a Gaussian Blur of each image frame. The definition of the sharpness signal 550 may be varied based on the application at hand. The maximum sharpness signal 560 may be defined as the highest sharpness value observed during the scan time. The maximum sharpness signal 560 is continually updated, and the derivative 570 of maximum sharpness is calculated over time. As shown in FIG. 8C, the derivative 570 of the maximum sharpness reaches a maximum at first position 544. When the derivative 570 of the maximum sharpness goes back to zero, this means that the best sharpness location has passed, and the controller C is triggered. For example, the controller C may be triggered at the second position 546, when the derivative 570 has settled at zero for a predefined number of steps. The first position 544 is deemed as the maximum sharpness position. Finally, the method 700 of FIG. 11 proceeds from block 720 to block 722, where the controller C is programmed to transmit the motor commands and move to the position for maximum sharpness.

The continuous autofocus mode 56 requires an initial set of starting values or estimates of the target location (in 3D space) and focal length. The starting values may be obtained when at least one of the disparity mode 50 or the sharpness control mode 52 has been successfully performed once during the application. In some embodiments, the continuous autofocus mode 56 will not function unless at least one of the disparity mode 50 or the sharpness control mode 52 has been completed. Alternatively, the initial set of starting values may be fed into the controller C as an output of a sub-routine or machine-learning algorithm. Subsequently, the continuous autofocus mode 56 measures relative changes in focal length and keeps the image in focus based on the deviations from the starting values, even as the robotic arm 24 is moving, and the target location, depth, and working distance may be changing.

The continuous autofocus mode 56 is independent of the movement of the robotic arm 24, which means it is monitoring the actual physical state of the robotic arm 24 and not the commands from the controller C (and/or robotic arm controller 42). This means that even in the presence of imperfect state tracking of the robotic arm 24, the image will still remain in focus.

The controller C of FIG. 1 may be an integral portion of, or a separate module operatively connected to the stereoscopic imaging platform 10. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic media, a CD-ROM, DVD, other optical media, punch cards, paper tape, other physical media with patterns of holes, a RAM, a PROM, an EPROM, a FLASH-EEPROM, other memory chips or cartridges, or other media from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The flowcharts presented herein illustrate an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based devices that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The numerical values of parameters (e.g., of quantities or conditions) in this specification, including the appended claims, are to be understood as being modified in each respective instance by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of each value and further divided ranges within the entire range. Each value within a range and the endpoints of a range are hereby disclosed as separate embodiments.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A stereoscopic imaging platform for imaging a target site, the stereoscopic imaging platform comprising:
    a stereoscopic camera configured to record a left image and a right image of the target site for producing at least one stereoscopic image of the target site;
    a robotic arm operatively connected to the stereoscopic camera, the robotic arm being adapted to selectively move the stereoscopic camera relative to the target site;
    wherein the stereoscopic camera includes a lens assembly having at least one lens and defining a working distance, the lens assembly having at least one focus motor adapted to move the at least one lens to selectively vary the working distance;
    a controller in communication with the stereoscopic camera and having a processor and tangible, non-transitory memory on which instructions are recorded;
    wherein the controller is adapted to selectively execute a continuous autofocus mode adapted to maintain a focus of the at least one stereoscopic image while the robotic arm is moving the stereoscopic camera and the target site is moving along at least an axial direction;
    wherein the controller is adapted to calculate an updated focal length at a current position of the target site based in part on a change in a target depth;
    wherein the controller is adapted to obtain the change in the target depth based on a closed-loop control module, and a difference between an initial target disparity at an initial target position and a current disparity value at the current position, the controller being adapted to execute the closed-loop control module to minimize the difference between the current disparity value and the initial target disparity; and
    the change in the target depth is determined as $[Kp(Rc-Rt)+Ki\int(Rc-Rt)dt-Kd*dRc/dt]$, where $Rc$ is the current disparity value, $Rt$ is the initial target disparity value, $t$ is time, $Kp$ is the proportional constant, $Ki$ is the integral constant, and $Kd$ is the derivative constant.

2. The stereoscopic imaging platform of claim 1, wherein: the controller is configured to determine a change in height of the stereoscopic camera from an initial camera position, the change in the height being defined as a displacement in position of the stereoscopic camera along the axial direction.

3. The stereoscopic imaging platform of claim 2, wherein: the change in the target depth is defined as the displacement in position of the target site along the axial direction.

4. The stereoscopic imaging platform of claim 1, wherein the controller is configured to obtain the disparity signal by:
    isolating an identifiable region in the left image;
    isolating a second region in the right image, the second region containing coordinates of the identifiable region and being larger than the identifiable region;
    performing a template match to obtain a pixel offset, the pixel offset being a horizontal displacement of the identifiable region in the left image and the identifiable region in the right image; and
    obtaining the disparity signal as the pixel offset at an optimal location of the template match.

5. The stereoscopic imaging platform of claim 1, wherein: the controller is configured to calculate the updated focal length based in part on the change in the height of the stereoscopic camera and the change in the target depth.

6. The stereoscopic imaging platform of claim 5, wherein calculating the updated focal length includes:
    obtaining the updated focal length F as a function of a first variable Zbase, a second variable z0 and a third variable z3 such that:

$$F = \left(\frac{Zbase - z0}{z3}\right);$$

wherein the first variable Zbase is a respective axial component of a current location of the target site in a robotic base frame;
    wherein the robotic base frame is transformable to a camera coordinate frame via a homogenous transformation matrix, the homogenous transformation matrix being composed of a rotational matrix and a translation vector; and
    wherein the second variable z0 is the respective axial component of the translation vector and the third variable z3 is the respective axial component of a column of the rotational matrix.

7. The stereoscopic imaging platform of claim 5, wherein:
    the controller is configured to calculate motor commands for the at least one focus motor corresponding to the updated focal length; and
    the controller is configured to transmit the motor commands to the at least one focus motor such that the working distance corresponds to the updated focal length.

8. The stereoscopic imaging platform of claim 7, wherein:
    when movement of the robotic arm is no longer detected, the controller is configured to determine the motor commands for the at least one focus motor corresponding to a maximum sharpness position; and wherein the maximum sharpness position is based on one or more sharpness parameters, including a sharpness signal, a maximum sharpness signal and a derivative over time of the maximum sharpness.

9. The stereoscopic imaging platform of claim 8, wherein:
the derivative of the maximum sharpness reaches a maximum at a first position, the derivative of the maximum sharpness moving from the first position and settling at approximately zero at a second position; and
the maximum sharpness position is defined as the first position.

10. The stereoscopic imaging platform of claim 8, wherein:
the sharpness signal is defined as a contrast between respective edges of an object in the at least one stereoscopic image; and
the maximum sharpness signal is defined as a largest sharpness value observed during a scan period.

11. The stereoscopic imaging platform of claim 8, wherein:
the at least one stereoscopic image includes one or more image frames; and
the sharpness signal is obtained by calculating a variance of a Laplacian of a Gaussian Blur of the one or more image frames.

12. The stereoscopic imaging platform of claim 8, wherein:
when movement of the robotic arm is no longer detected, the controller is configured to command the focus motor to the maximum sharpness position.

13. A robotic imaging platform for imaging a target site, the robotic imaging platform comprising:
a stereoscopic camera configured to record left and right images of the target site for producing at least one stereoscopic image of the target site;
a robotic arm operatively connected to the stereoscopic camera, the robotic arm being adapted to selectively move the stereoscopic camera relative to the target site;
wherein the stereoscopic camera includes a lens assembly having at least one lens and defining a working distance, the lens assembly having at least one focus motor adapted to move the at least one lens to selectively vary the working distance;
a controller in communication with the stereoscopic camera and having a processor and tangible, non-transitory memory on which instructions are recorded;
wherein the controller is adapted to selectively execute a continuous autofocus mode adapted to maintain a focus of the at least one stereoscopic image while the robotic arm is moving the stereoscopic camera and the target site is moving along at least an axial direction; and
wherein the continuous autofocus mode is adapted to determine respective deviations from a set of starting values, the set of starting values including an initial camera position and an initial target position, the respective deviations include a change in target depth from the initial target position;
wherein the controller is adapted to calculate an updated focal length at a current position of the target site based in part on the change in the target depth;
wherein the controller is adapted to obtain the change in the target depth based on a closed-loop control module, and a difference between an initial target disparity at the initial target position and a current disparity value at the current position, the controller being adapted to execute the closed-loop control module to minimize the difference between the current disparity value and the initial target disparity; and
wherein the closed-loop control module is a proportional-integral-derivative control module defining a proportional constant, an integral constant and a derivative constant, the change in the target depth being determined as $[K_p(R_c-R_t)+K_i\int(R_c-R_t)dt-K_d*dR_c/dt]$, where Rc is the current disparity value, Rt is the initial target disparity value, t is time, Kp is the proportional constant, Ki is the integral constant, and Kd is the derivative constant.

14. The robotic imaging platform of claim 13, wherein:
the one or more automatic focusing modes includes at least one of a disparity mode and a sharpness control mode; and
the set of starting values is obtained from at least one of the disparity mode and the sharpness control mode executed prior to the continuous autofocus mode.

15. The robotic imaging platform of claim 13, wherein:
the respective deviations include a change in height of the stereoscopic camera from the initial camera position, the change in the height being defined as a displacement in position of the stereoscopic camera along the axial direction; and
the change in the target depth is defined as the displacement in position of the target site along the axial direction.

16. The robotic imaging platform of claim 15, wherein:
the controller is configured to calculate the updated focal length based in part on the change in the height of the stereoscopic camera and the change in the target depth.

17. The robotic imaging platform of claim 16, wherein:
when movement of the robotic arm is no longer detected, the controller is configured to determine motor commands for the at least one focus motor corresponding to a maximum sharpness position; and
wherein the maximum sharpness position is based on one or more sharpness parameters, including a sharpness signal, a maximum sharpness signal and a derivative over time of the maximum sharpness.

* * * * *